(12) United States Patent
Rodriguez et al.

(10) Patent No.: US 7,077,977 B2
(45) Date of Patent: Jul. 18, 2006

(54) BULKY BORATE ACTIVATIONS

(75) Inventors: George Rodriguez, Houston, TX (US);
Francis C. Rix, League City, TX (US);
Matthew C. Kuchta, Houston, TX (US); John F. Walzer, Jr., Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 42 days.

(21) Appl. No.: 10/497,741

(22) PCT Filed: Dec. 3, 2002

(86) PCT No.: PCT/US02/38470

§ 371 (c)(1),
(2), (4) Date: Jun. 4, 2004

(87) PCT Pub. No.: WO03/049856

PCT Pub. Date: Jun. 19, 2003

(65) Prior Publication Data

US 2004/0254065 A1 Dec. 16, 2004

Related U.S. Application Data

(60) Provisional application No. 60/336,671, filed on Dec. 5, 2001.

(51) Int. Cl.
*B01J 31/14* (2006.01)
*C08F 4/12* (2006.01)
*C08F 4/14* (2006.01)
*C08F 110/00* (2006.01)

(52) U.S. Cl. .................. 252/182.15; 252/182.18; 252/182.29; 502/103; 502/108; 502/117; 502/152; 502/202; 526/127; 526/160; 526/351; 568/6

(58) Field of Classification Search ............ 252/182.15
See application file for complete search history.

(56) References Cited

U.S. PATENT DOCUMENTS

| | | | |
|---|---|---|---|
| 4,871,705 A | 10/1989 | Hoel ................... | 502/117 |
| 5,198,401 A | 3/1993 | Turner et al. .......... | 502/155 |
| 5,278,119 A | 1/1994 | Turner et al. .......... | 502/155 |
| 5,278,264 A | 1/1994 | Spaleck et al. ........ | 526/127 |
| 5,296,433 A | 3/1994 | Siedle et al. .......... | 502/117 |
| 5,447,895 A | 9/1995 | Marks et al. .......... | 502/117 |
| 5,502,017 A | 3/1996 | Marks et al. .......... | 502/103 |
| 6,255,531 B1 * | 7/2001 | Fritz et al. ............ | 568/3 |
| 6,300,450 B1 * | 10/2001 | Tsujimoto et al. ..... | 526/335 |
| 6,391,989 B1 | 5/2002 | Bohnen et al. ........ | 526/134 |
| 6,541,410 B1 * | 4/2003 | Rodriguez ............ | 502/103 |
| 6,774,253 B1 * | 8/2004 | Resconi ............... | 556/11 |
| 6,872,844 B1 * | 3/2005 | Vogel .................. | 556/1 |
| 6,909,008 B1 * | 6/2005 | Rodriguez ............ | 556/9 |
| 2002/0082161 A1 * | 6/2002 | Vogel .................. | 502/154 |

FOREIGN PATENT DOCUMENTS

| | | |
|---|---|---|
| EP | 0 277 003 | 1/1987 |
| EP | 0 277 004 | 1/1987 |
| EP | 824 113 A | 8/1997 |
| EP | 0 811 627 | 12/1997 |
| WO | 97/29845 | 8/1997 |
| WO | WO 99/42467 | 8/1999 |

OTHER PUBLICATIONS

Ahlers et al., "Dynamic Features of the Zirconocene-Boron=betaine complexes obtained by treatment of bis(alkynyl) zirconocenes with the tris(pentafluorophenyl) borane Lewis-acid," Journal of Organometallic Chemistry, vol. 527, No. 1, pp. 191-201, (Jan. 11, 1997).

Kropp et al., "Photochemistry of Alkynyl-, Alkenyl-, and Cyclopropyl-Substituted Borate Salts: The Di-π-and Cyclopropyl-π-borate Rearrangements", J. Am. Chem. Soc., vol. 113, pp. 2155-2163 (1991).

Baird et al., J. Am. Chem. Soc. vol. 116, pp. 6435-6436 (1994).

Strauss, Steven. "The Search for Larger and More Weakly Coordinating Anions," Chem. Rev. vol. 93, pp. 927-942 (1993).

Han et al., "Tetraorganogallate Complexes in Organic Chemistry: A Novel, Efficient and Versatile Preparation of Ketones from Acyl Chlorides", Tetrahedron Letters, Elsevier Science Publishers, Amsterdam, NL, vol. 36, No. 8, pp. 1287-1290 (Feb. 20, 1995).

* cited by examiner

*Primary Examiner*—Joseph D. Anthony
(74) *Attorney, Agent, or Firm*—Catherine L. Bell

(57) ABSTRACT

A discrete polyolefin catalyst activator is disclosed. A salient feature of invention borate-based activators is that at least one of the ligands on the borate non-coordinating anion (NCA) comprises a fluorinated aryl group linked to the boron atom through an acetylenic group appropriate pairing of invention activators with olefin polymerization. Catalyst precursors yield increased catalytic activity. Polymerization results are disclosed.

46 Claims, No Drawings

BULKY BORATE ACTIVATIONS

CROSS REFERENCE TO RELATED APPLICATIONS

This application is a National Stage Application of International Application No. PCT/US02/38470, filed Dec. 3, 2002, which claims the benefit of Provisional Application No. 60/336,671, filed Dec. 5, 2001.

FIELD OF INVENTION

This invention relates to polymerization cocatalyst compounds containing weakly coordinating Group-13-element anions and to the preparation of olefin polymers using ionic catalyst systems based on organometallic transition-metal cationic compounds stabilized by these anions.

BACKGROUND OF THE INVENTION

The term "noncoordinating anion"(NCA) is now accepted terminology in the field of olefin and vinyl molecule, coordination, insertion, and carbocationic polymerization. See, for example, EP 0 277 003, EP 0 277 004, U.S. Pat. No. 5,198,401, U.S. Pat. No. 5,278,119, and Baird, Michael C., et al, *J. Am. Chem. Soc.* 1994, 116, 6435–6436. The non-coordinating anions are described to function as electronic stabilizing cocatalysts, or counterions, for active, cationic metallocene polymerization catalysts. The term noncoordinating anion applies both to truly noncoordinating anions and to coordinating anions that are labile enough to undergo replacement by olefinically or acetylenically unsaturated molecules at the insertion site. These noncoordinating anions can be effectively introduced into a polymerization medium as Bronsted acid salts containing charge-balancing countercations, as ionic cocatalyst compounds, or mixed with an organometallic catalyst before addition to the polymerization medium. See also, the review articles by S. H. Strauss, "The Search for Larger and More Weakly Coordinating Anions", *Chem. Rev.*, 93, 927–942 (1993).

U.S. Pat. No. 5,502,017, to Marks et al., addresses ionic metallocene catalysts for olefin polymerization containing a weakly coordinating anion comprising boron substituted with halogenated aryl substituents preferably containing silylalkyl substitution, such as a t-butyldimethyl-silyl substitution. Marks et al. disclose the weakly coordinating anion as the cocatalyst. The silylalkyl substitution is said to increase the solubility and thermal stability of the resulting metallocene salts. Examples 3–5 describe synthesis of and polymerization with the cocatalyst compound triphenylcarbenium tetrakis (4-dimethyl-t-butylsilyl-2,3,5,6-tetrafluorophenyl) borate.

In view of the above, there is a continuing need for olefin polymerization activators both to improve the industrial economics of solution polymerization and to provide alternative activating compounds for ionic, olefin polymerization catalyst systems.

SUMMARY OF THE INVENTION

The invention comprises a discrete catalyst activator (also known as a cocatalyst). This activator abstracts a ligand from an olefin-polymerization-catalyst precursor to yield a catalyst containing a cationic site. The activator also leaves behind a counterion to charge balance the catalyst: a non-coordinating anion. Invention non-coordination anions comprise a triel connected to at least one bulky aryl ligand, such as biphenyl, and to at least one anion-forming ligand. The anion-forming ligand comprises an aryl ring in which one ring hydrogen has been replaced by a spacing group. This ligand connects to the triel atom through the spacing group.

In another embodiment, invention non-coordination anions comprise a Group-13 atom connected to at least one ring assembly, such as biphenyl, and to at least one ligand containing an acetylenic-group and any aryl group. This ligand connects to the Group-13 atom through the acetylenic carbon distal to the aryl ring. The NCA portion comprising the acetylenic group is sometimes referred to as an "acetyl-aryl" moiety. The distinguishing feature of these invention NCA embodiments is the presence of an acetylenic functional group connected to a Group-13 atom. The Group-13 atom also connects to at least one fluorinated ring moiety: monofluorinated up through perfluorinated. In addition to a first ring moiety, the Group-13 atom has two other ligands that may also be ring moieties similar to or different from the first ring moiety and may be monofluorinated to perfluorinated.

The invention encompasses catalysts made with this cocatalyst, cocatalyst systems composed of this cocatalyst, olefin polymerization methods using this cocatalyst, articles of manufacture made from these polyolefins, and methods of preparing this cocatalyst.

DETAILED DESCRIPTION OF THE INVENTION

Definitions

The term "hydrocarbyl radical" is sometimes used interchangeably with "hydrocarbyl" throughout this document. For purposes of this disclosure, "hydrocarbyl radical" encompasses $C_1$–$C_{50}$ radicals. These radicals can be linear, branched, or cyclic, and when cyclic, aromatic or non-aromatic. Thus, the term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which at least one hydrogen atom has been substituted with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, $NR''$, $PR''$, $BR''$, $SiR''_2$, $GeR''_2$, and the like, where R" is independently a hydrocarbyl or halocarbyl radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, $NR''$, $PR''$, $BR''$, $SiR''_2$, $GeR''_2$, and the like where R" is independently a hydrocarbyl or halocarbyl radical provided that at least one halogen atom remains on the original halocarbyl radical.

In some embodiments, the hydrocarbyl radical is independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. The radical may then be subjected to the types of substitutions described above.

For purposes of this disclosure, triel (Tr) represents boron and aluminum.

Description

Invention cocatalysts or activiators comprise a cation-non-coordinating-anion pair. The main feature of the cation is that it is capable of abstracting a ligand from the catalyst precursor, which results in catalyst activation. Such a cation is sometimes referred to as an activating cation. The main feature of the non-coordinating anion is that it is substanatially non-coordinating to the activated polymerization catalyst. Substantially non-coordinating means that the anion does not coordinate to the activated catalyst or, if it does coordinate to the catalyst, it does so weakly enough that incoming olefin monomer can displace it. Greater-coordinating-strength anions suit invention cocatalysts less than lower-coordinating strength ones.

Tr stands for triel, which, for this disclosure, encompasses B and Al. When Tr=B, this NCA is called tris(2',3,3',4,4',5,5',6,6'-nonafluorobiphen-2-yl)(2-perfluorophenylethyn-1-yl)borate.

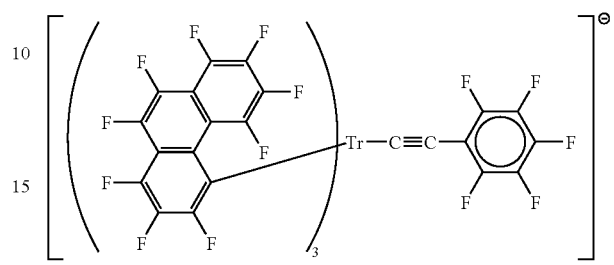

When Tr=B, this NCA is called tris(1,2,3,5,6,7,8,9,10-nonafluorophenanthra-4-yl)(2-perfluorophenylethyn-1-yl)borate.

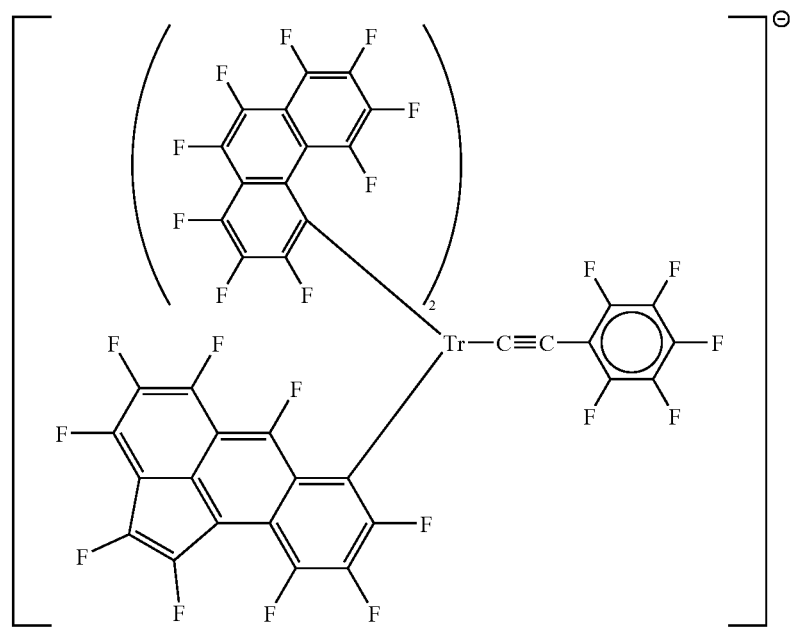

When Tr=B, this NCA is called bis(1,2,3,5,6,7,8,9,10-nonafluorophenanthra-4-yl)(1,2,3,4,5,6,8,9,10-nonafluoro-aceanthra-7-yl)(2-perfluorophenylethyn-1-yl)borate.

Invention non-coordinating anions share a common feature: they contain bulky aryl ligands on the triel that sterically encumber the triel. Bulky aryl ligands are aryl-containing ligands with such a size and geometry that, after three of them attach to the triel, the triel is unable to accommodate direct connection to a fourth bulky ligand. Thus, the size and geometry of the bulky aryl ligands resist triel anion formation. To proceed with forming an anion under these conditions, invention NCAs comprise a group that can attach to the triel despite the impediment formed by the bulky aryl groups.

Exemplary invention NCAs are shown below.

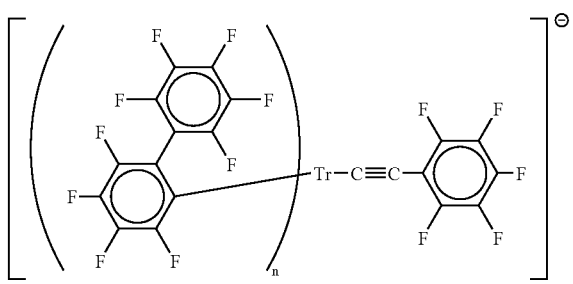

This final ligand comprises a capping group (described below) and a spacing group. Including a spacing group as part of this ligand allows the triel anion to form. Invention NCAs use a reactive spacing group: by its nature, it can migrate to or react with the catalyst precursor or activated catalyst unless used as described below. This final ligand is referred to as an anion-forming ligand because, after it is added to the triel-bulky-aryl-ligand complex, an anionic complex forms.

While useful in this invention, the spacing group's reactivity typically makes it unsuitable for use with many early-transition-metal-based catalysts. It is unsuitable because it can terminate catalysis at the metal center and thereby decrease the system's overall activity and productivity. One of ordinary skill recognizes that once the system's activity or productivity has decreased enough, the catalyst system is no longer suitable for commercial use.

While the spacing group is sometimes unsuitable for use with early transition-metal catalysts, it suits invention NCAs. Without wishing to be bound by any theory, the bulky aryl ligands on the triel shield the reactive portion of the spacing group. Therefore, when the spacing group is combined with the capping group described below and used with the encumbered triel described above, it enables anion formation without unduly decreasing catalyst activity or productivity. Thus, another distinguishing aspect of some embdiments of invention NCAs is the anion-forming ligand combined with three bulky aryl ligands.

For the most part, bulky aryl ligands comprise side groups or fused rings adjacent to the ligand-triel connection. As stated above, whatever the choice of side groups or fused ring on the bulky aryl ligand, the ligand must provide sufficient bulk, when combined with two other bulky ligands, to impede direct connection of another bulky ligand and sufficient bulk to shield the spacing group. Bulky aryl ligands, when fluorinated, are sometimes represented as $Ar_f$ in this document.

Suitable bulky aryl ligands include, but are not limited to, the following groups. These groups are shown as homoatomic rings or ring systems and are shown without fluorine substitution. Thus, the depicted groups do not necessarily function with this invention. These groups should be fluorinated to one degree or another and may be modified to contain a heteroatom within the ring or ring system. Bulky aryl ligands may comprise one or more heteroatoms within a ring or ring system and do contain at least one fluorine substitution on a ring system. Some embodiments select at least one bulky aryl ligand to be substantially fluorinated. Some embodiments select at least one bulky aryl ligand to be perfluorinated.

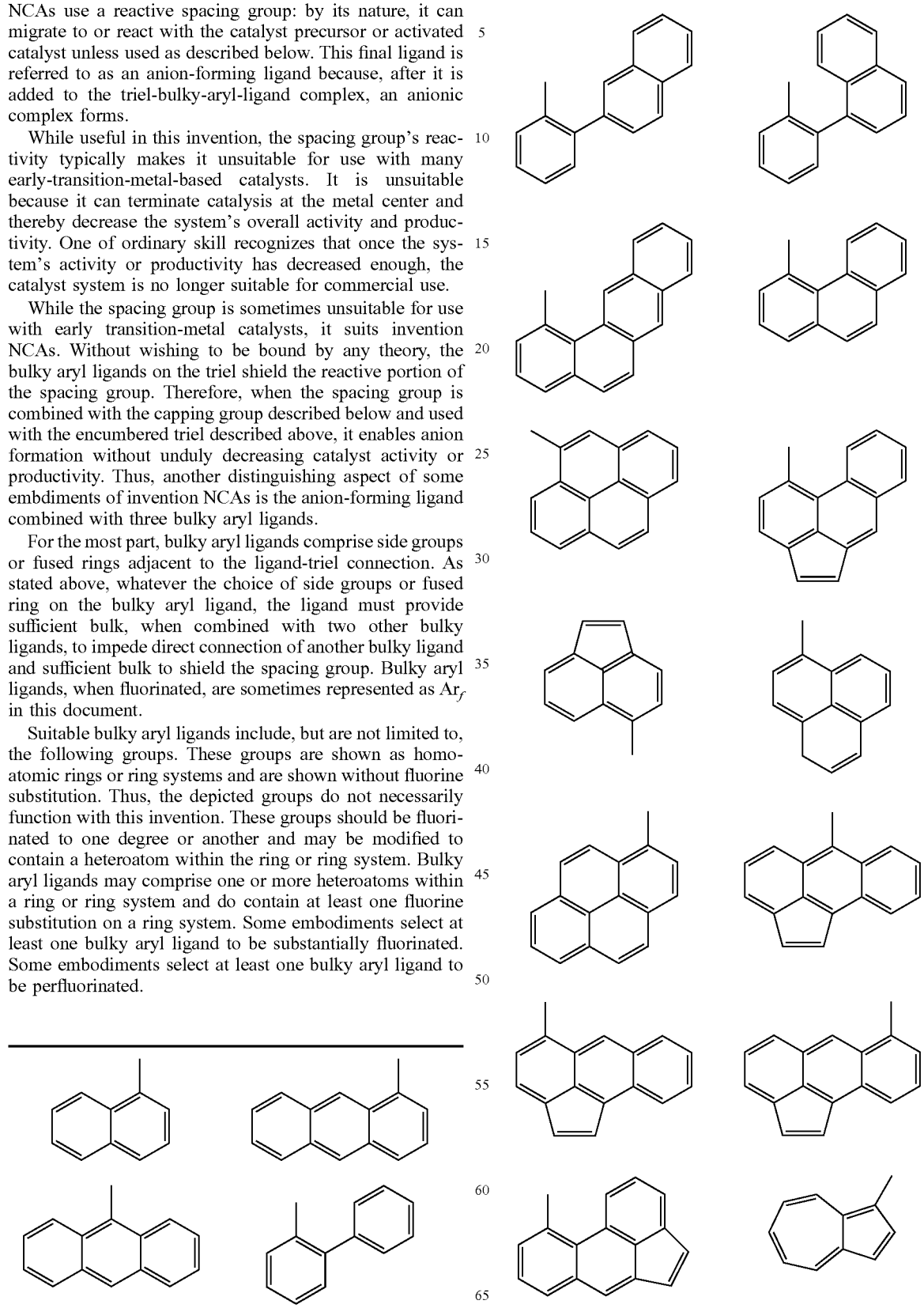

-continued

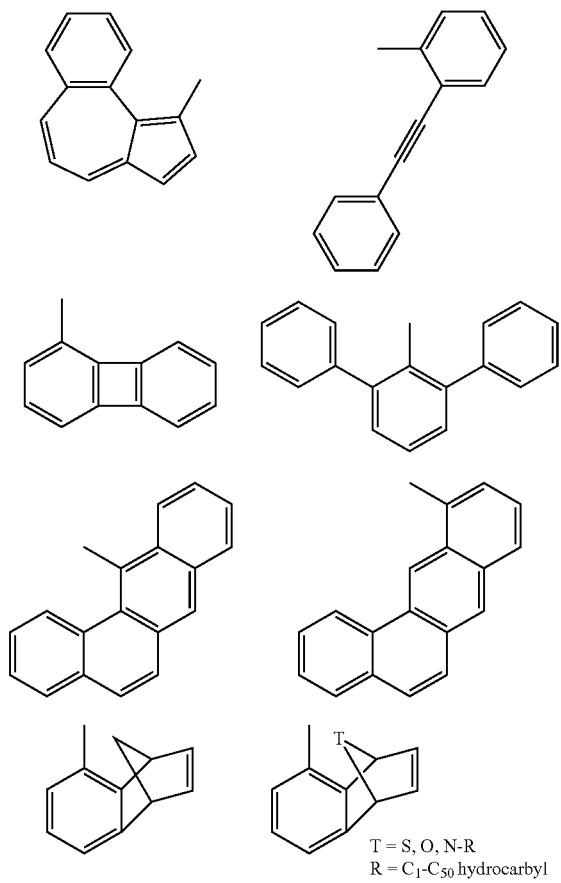

T = S, O, N-R
R = C$_1$-C$_{50}$ hydrocarbyl

Depending on the choice of the other bulky aryl ligands, the following ligands can serve as bulkyl aryl ligands. Phenyl, biphenyl, naphthyl, indenyl, anthracyl, fluorenyl, azulenyl, phenanthrenyl, and pyrenyl are suitable aryl radicals. Some embodiments select phenyl, biphenyl, or naphthyl as the aryl radicals. Exemplary Ar$_f$ ligands and Ar$_f$ substituents useful in this invention specifically include the fluorinated species of these aryl radicals. Perfluorinated aryl groups also function and include substituted Ar$_f$ groups having substituents in addition to fluorine, such as fluorinated hydrocarbyl groups. The disclosures of U.S. Pat. Nos. 5,198,401, 5,296,433, 5,278,119, 5,447,895, 5,688,634, 5,895,771, WO 93/02099, WO 97/29845, WO 99/43717, WO 99/42467 and copending U.S. application Ser. No. 09/261,627, filed 3 Mar. 1999, and its equivalent WO 99/45042 teach suitable Ar$_f$ groups. Generally, fluorination encompasses adding a fluorine atom to the aryl ligand including adding a hydrocarbyl group that itself comprises a fluorine atom.

Perfluorinated means that each aryl hydrogen atom is substituted with fluorine or fluorcarbyl substituents, e.g., trifluoromethyl, pentafluoroethyl, heptafluoro-isopropyl, tris (trifluoromethyl)silyltetrafluoroethyl, and bis(trifluoroethyl) (heptafluoropropyl)silyltetrafluoroethyl.

The goal of aryl-ligand fluorination is to remove abstractable hydrogen from the NCA. Therefore, any ligand choice or substitution pattern that minimizes the number of abstractable hydrogen is useful in this invention's practice. Thus, suitable ligand choices and substitution patterns will depend somewhat on the selected catalyst. If abstractable hydrogen is present, either the activator or the activated catalyst may abstract the hydrogen. This causes the catalyst system's activity or productivity to decrease or requires an excess of activator. One of ordinary skill recognizes that once the system's activity or productivity has decreased enough, the catalyst system is no longer suitable for commercial use. Thus, one of ordinary skill recognizes that not all hydrogen substituents must be fluorine-replaced. One of ordinary skill recognizes that some hydrogen may remain as long as those hydrogen do not unacceptably compromise the commercial utility of the catalyst system, in the estimation of one of ordinary skill. Substantially non-abstractable means that hydrogen may be extractable but at levels low enough so that the degree of chain termination and catalyst poisoning remains below that which one of ordinary skill finds commercially acceptable. Some embodiments target lesser levels of abstractability.

Anion-forming ligands comprise a spacing group and a capping group. The spacing group functions to offset the bulkiness of the capping group from the triel. To accomplish this the spacing group should be shaped such that in two directions it has a small enough cross section to access the triel despite the bulky aryl ligands.

One of ordinary skill recognizes that the geometry around the triel defines a minimum distance between the capping group and the triel. The spacing group should be long enough to cross this distance so that it can attach the capping group to the triel.

An example of a suitable spacing group is —C≡C—.

Capping groups should have enough bulk so that the NCA remains substantially non-coordinating as that term is defined above. They should also have enough bulk to shield the spacing group. One of ordinary skill recognizes, after being taught this invention, that any number of ligands will function as the capping group. They will also recognize that certain choices of capping group may make some choices of spacing group unavailable. For instance, a particularly large capping group may need a longer spacing group. Some invention embodiments select the capping group to comprise an aryl group. Of those, some embodiments select the aryl group to be fluorinated, substantially fluorinated, or perfluorinated; some embodiments replace at least one-third of the hydrogen atoms connected to aromatic ligands with fluorine. Ligands that function as bulky aryl ligands are expected to function as capping groups.

Useful capping groups may comprise the following aryl ligands: fluorophenyl, perfluorophenyl, 3,5-bis(trifluoromethyl)phenyl, trifluorophenyl, (trifluoromethyl)phenyl, naphth-1-yl, naphth-2-yl, perfluoronaphth-1-yl, perfluoronaphth-2-yl, (trifluoro)naphth-1-yl, (trifluoro)naphth-2-yl, (trifluoromethyl)naphth-1-yl, (trifluoromethyl)naphth-2-yl, anthr-1-yl, anthr-2-yl, perfluoroanthr-1-yl, perfluoroanthr-2-yl, (trifluoro)anthr-1-yl, (trifluoro)anthr-2-yl, (trifluoromethyl)anthr-1-yl, (trifluoromethyl)anthr-2-yl, phenanthr-1-yl, phenanthr-2-yl, perfluorophenanthr-1-yl, perfluorophenanthr-2-yl, (trifluoro)phenanthr-1-yl, (trifluoro)phenanthr-2-yl, (trifluoromethyl)phenanthr-1-yl, (trifluoromethyl)phenanthr-2-yl, biphen-3-yl, biphen-4-yl, perfluorobiphen-3-yl, perfluorobiphen-4-yl, (trifluoro)biphen-3-yl, (trifluoro)biphen-4-yl, (trifluoromethyl)biphen-3-yl, and (trifluoromethyl)biphen-4-yl.

Also, useful capping groups may comprise the aryl ligands described or depicted above as bulky aryl groups. Thus, for the anion-forming ligand a bulky aryl group connected to a spacing group is within the invention's scope.

The cationic portion of invention activators has the form $R_3PnH$, wherein R represents an alkyl or aryl moiety; Pn represents a pnictide: N, P, or As; and H is hydrogen. Suitable R are shown below. This list does not limit the scope of the invention; any R that allows the cationic portion to function as described is within the scope of this invention. R includes, but is not limited to, methyl, phenyl, ethyl, propyl, butyl, hexyl, octyl, nonyl, 3-ethylnonyl, isopropyl, n-butyl, cyclohexyl, benzyl. R also includes any hydrocarbyl-substituted versions of the foregoing and any fluorocarbyl or fluorohydrocarbyl substitution on the foregoing.

Catalyst precursor compounds suitable for use in this invention include the known organometallic, transition metal compounds useful for traditional Ziegler-Natta polymerization, particularly the metallocenes known to be useful in polymerization. The catalyst precursor must be susceptible to activation by invention cocatalysts. Useful catalyst precursors include Group-3–10 transition metal compounds in which at least one metal ligand that is abstractable by the cocatalyst. Particularly, those abstractable ligands include hydride, hydrocarbyl, hydrocarbylsilyl, and their lower-alkyl-substituted ($C_1$–$C_{10}$) derivatives. Examples include hydride, methyl, benzyl, dimethyl-butadiene, etc. Abstractable ligands and transition metal compounds comprising them include those metallocenes described in, for example, U.S. Pat. No. 5,198,401 and WO 92/00333. Syntheses of these compounds are well known from the published literature. Additionally, in those cases where the metal ligands include labile halogen, amido, or alkoxy ligands (for example, biscyclopentadienyl zirconium dichloride), which may not allow for ready abstraction with this invention's cocatalysts, the labile ligands can first be replaced with abstractable ones. This replacement uses known routes such as alkylation with lithium or aluminum hydrides, alkyls, alkylalumoxanes, Grignard reagents, etc. See also EP 0 500 944 and EP 0 570 982 for the reaction of organoaluminum compounds with dihalo-substituted metallocenes before catalyst activation.

Additional descriptions of metallocene compounds with, or that can be alkylated to contain, at least one ligand abstractable to form catalytically active transition-metal cations appear in the patent literature. (E.g., EP-A-0 129 368, U.S. Pat. Nos. 4,871,705, 4,937,299, 5,324,800, 5,470, 993, 5,491,246, 5,512,693, EP-A-0 418 044, EP-A-0 591 756, WO-A-92/00333, WO-A-94/01471 and WO 97/22635.) Such metallocenes can be described as mono- or biscyclopentadienyl-substituted Group-3, -4, -5, or -6 transition metals. The transition metal ligands may themselves be substituted with one or more groups, and the ligands may bridge to each other or bridge through a heteroatom to the transition metal. The size and constituency of the ligands and bridging elements should be chosen in the literature-described manner to enhance activity and to select desired characteristics. Embodiments in which the cyclopentadienyl rings (including substituted, cyclopentadienyl-based, fused-ring systems, such as indenyl, fluorenyl, azulenyl, or their substituted analogs), when bridged to each other, are lower-alkyl substituted ($C_1$–$C_6$) in the 2 position (with or without a similar 4-position substituent in the fused ring) are useful. The cyclopentadienyl rings may additionally comprise alkyl, cycloalkyl, aryl, alkylaryl, and arylalkyl substituents, the latter as linear, branched, or cyclic structures including multi-ring structures, for example, those of U.S. Pat. Nos. 5,278,264 and 5,304,614. In some embodiments, such substituents should each have essentially hydrocarbyl characteristics and will typically contain up to 30 carbon atoms, and may contain heteroatoms, such as 1 to 5 non-hydrogen or non-carbon atoms, e.g., N, S, O, P, Ge, B and Si.

Invention activators are useful with essentially all known metallocene catalyst that are suitable for preparing linear polyethylene, linear polypropylene, or ethylene- or propylene-containing copolymers (where copolymer means a polymer prepared using at least two different monomers). (See WO-A-92/00333 and U.S. Pat. Nos. 5,001,205, 5,198, 401, 5,324,800, 5,304,614 and 5,308,816.) Criteria for selecting suitable metallocene catalysts for making polyethylene and polypropylene are well known in the art, in both patent and academic literature, see for example *Journal of Organometallic Chemistry* 369, 359–370 (1989). Likewise, methods for preparing these metallocenes are also known. Typically, the catalysts are stereorigid, asymmetric, chiral, or bridged-chiral metallocenes. See, for example, U.S. Pat. No. 4,892,851, U.S. Pat. No. 5,017,714, U.S. Pat. No. 5,296,434, U.S. Pat. No. 5,278,264, WO-A-(PCT/US92/ 10066)WO-A-93/19103, EP-A2-0 577 581, EP-A1-0 578 838, and academic literature "The Influence of Aromatic Substituents on the Polymerization Behavior of Bridged Zirconocene Catalysts", Spaleck, W., et al, *Organometallics* 1994, 13, 954–963, and "ansa-Zirconocene Polymerization Catalysts with Annelated Ring Ligands-Effects on Catalytic Activity and Polymer Chain Lengths", Brinzinger, H., et al, *Organometallics* 1994, 13, 964–970, and documents referred to therein. Though many of these references deal with alumoxane-activated catalyst systems, analogous metallocenes can be activated with this invention's cocatalysts. In catalyst systems lacking abstractable ligands, at least one non-abstractable ligand must first be replaced with an abstractable one. Replacement by alkylation, as described above, is one example. Additionally, the metallocenes should contain a group into which an ethylene or α-olefin group, —C=C—, may insert, for example, hydride, alkyl, alkenyl, or silyl. See additional description in G. G. Hlatky, "Metallocene catalysts for olefin polymerization Annual review of 1996", Coordination Chemistry Reviews, 181, 243–296 (Elsevier Science, 1999).

Representative metallocene compounds can have the formula:

$$L_A L_B L_{Ci} MDE$$

where M is a Group-3–10 metal; $L_A$ is a substituted or unsubstituted, cyclopentadienyl or heterocyclopentadienyl ligand connected to M; and $L_B$ is a ligand as defined for $L_A$, or is J, a heteroatom ligand connected to M. $L_A$ and $L_B$ may connect to each other through a Group-13–16-element-containing bridge. $L_{Ci}$ is an optional, neutral, non-oxidizing ligand connected to M (i equals 0 to 3); and D and E are the same or different labile ligands, optionally bridged to each other, $L_A$, or $L_B$. Each of D and E are connected to M. Some embodiments select M to be a member of the Group-3–6 transition metals. Other embodiments select M to be a Group-4 transition metal. Some embodiments select M to be Ti, Zr, or Hf.

$L_A$ and $L_B$ are sometimes called ancillary ligands because they are believed to help the metal center retain the correct electronic and geometric structure from olefin polymerization.

Function constrains D and E in at least two ways: (1) upon activation, either the D-M or E-M connection must break; and (2) monomer must be able to insert between whichever of D-M or E-M remains. D and E should be chosen to maximize these functions.

Cyclopentadienyl also encompasses fused-ring systems including but not limited to indenyl and fluorenyl radicals. Also, the use of heteroatom-containing rings or fused rings, where a non-carbon, Group-13, -14, -15, or -16 atom replaces a ring carbon is within the term "cyclopentadienyl" for this specification. See, for example, the background and illustrations of WO 98/37106, having priority with U.S. Ser. No. 08/999,214, filed Dec. 29, 1997, and WO 98/41530, having priority with U.S. Ser. No. 09/042,378, filed Mar. 13, 1998. Substituted cyclopentadienyl structures are structures in which one or more hydrogen atoms are replaced by a hydrocarbyl, hydrocarbylsilyl, or similar heteroatom-containing structure. Hydrocarbyl structures specifically include $C_1$–$C_{30}$ linear, branched, and cyclic alkyl, and aromatic fused and pendant rings. These rings may also be substituted with ring structures.

Catalyst precursors also include the mono- and biscyclopentadienyl compounds such as those listed and described in U.S. Pat. Nos. 5,017,714, 5,324,800, and WO 92/00333 and EP-A-0 591 756.

Bis amide catalyst precursors are useful with invention cocatalysts. Bisamide catalyst precursors are those precursors that have the following formula:

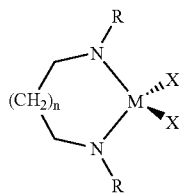

M is Ti, Zr, or Hf. R are the same or different alkyl, aryl, substituted alkyl, or substituted aryl radicals. X are the same or different alkyl, aryl, or halide radicals. Substituted alkyls and aryls can be alkyl-, aryl-, and halo-substituted. When X is a halide, the bisamide catalyst precursor must first be chemically modified to transform X into an abstractable ligand. This can be done by alkylation, for example.

Pyridine bisamide catalyst precursors are also useful with invention co-catalysts. Pyridine bisamide catalyst precursors are those precursors that have the following formula:

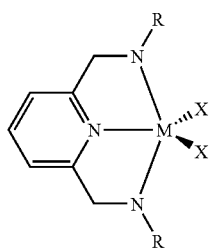

M is Ti, Zr, or Hf. R are the same or different alkyl, aryl, substituted alkyl, or substituted aryl radicals. X are the same or different alkyl, aryl, or halide radicals. Substituted alkyls and aryls can be alkyl-, aryl-, and halo-substituted. When X is a halide, the pyridine bisamide catalyst precursor must first be chemically modified to transform X into an abstractable ligand. This can be done by alkylation, for example.

Amine bisamide catalyst precursors are also useful with invention co-catalysts. Amine bisamide catalyst precursors are those precursors that have the following formula:

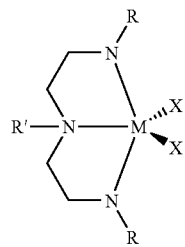

M is Ti, Zr, or Hf. R and R' are the same or different alkyl, aryl, substituted alkyl, or substituted aryl radicals. X are the same or different alkyl, aryl, or halide radicals. Substituted alkyl and aryls can be alkyl-, aryl-, and halo-substituted. When X is a halide, the amine bisamide catalyst precursor must first be chemically modified to transform X into an abstractable ligand. This can be done by alkylation, for example.

Additional exemplary metallocene-type catalysts include those metallocene compounds represented by the formula:

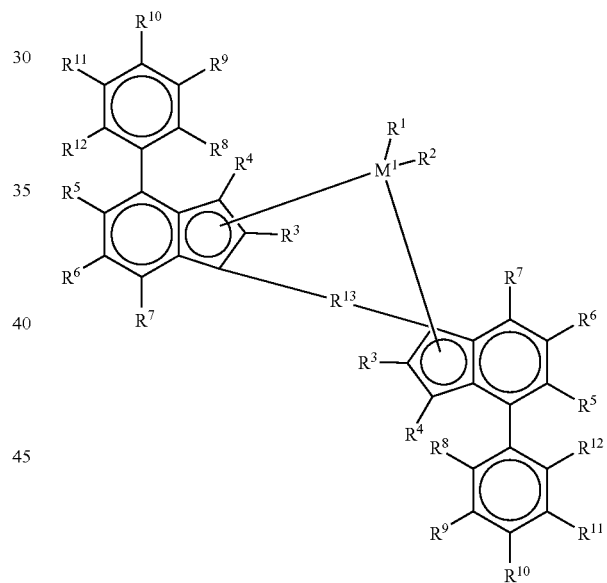

In the above structure, $M^1$ is selected from titanium, zirconium, hafnium, vanadium, niobium, tantalum, chromium, molybdenum, or tungsten.

$R^1$ and $R^2$ are identical or different and are selected from hydrogen atoms, $C_1$–$C_{10}$ alkyl groups, $C_1$–$C_{10}$ alkoxy groups, $C_6$–$C_{10}$ aryl groups, $C_6$–$C_{10}$ aryloxy groups, $C_2$–$C_{10}$ alkenyl groups, $C_2$–$C_{40}$ alkenyl groups, $C_7$–$C_{40}$ arylalkyl groups, $C_7$–$C_{40}$ alkylaryl groups, $C_8$–$C_{40}$ arylalkenyl groups, OH groups or halogen atoms; or conjugated dienes that are optionally substituted with one or more hydrocarbyl, tri(hydrocarbyl)silyl groups or hydrocarbyl, tri(hydrocarbyl) silylhydrocarbyl groups. The conjugated diene can contain up to 30 atoms not counting hydrogen.

$R^3$ are the same or different and are selected from hydrogen atom, halogen atoms, $C_1$–$C_{10}$ halogenated or unhalogenated alkyl groups, $C_6$–$C_{10}$ halogenated or unhalogenated aryl groups, $C_2$–$C_{10}$ halogenated or unhalogenated alkenyl groups, $C_7$–$C_{40}$ halogenated or unhalogenated arylalkyl groups, $C_7$–$C_{40}$ halogenated or unhalogenated alkylaryl groups, $C_8$–$C_{40}$ halogenated or unhalogenated arylalkenyl groups, —NR'$_2$, —SR', —OR', —OSiR'$_3$ or —PR'$_2$ radicals in which R' is one of a halogen atom, a $C_1$–$C_{10}$ alkyl group, or a $C_6$–$C_{10}$ aryl group.

$R^4$ to $R^7$ are the same or different and are hydrogen, as defined for $R^3$ or two or more adjacent radicals $R^5$ to $R^7$ together with the atoms connecting them form one or more rings.

$R^{13}$ is selected from

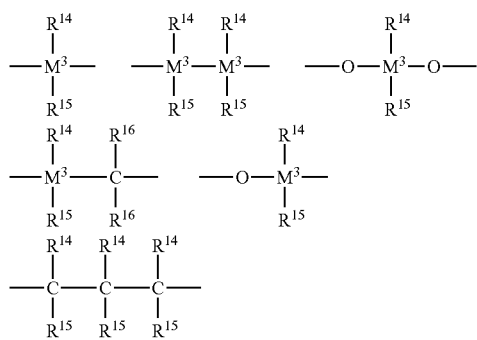

—B($R^{14}$)—, —Al($R^{14}$)—, —Ge—, —Sn—, —O—, —S—, —SO—, —SO$_2$—, —N($R^{14}$)—, —CO—, —P($R^{14}$)—, —P(O)($R^{14}$)—, —B(N$R^{14}R^{15}$)— and —B[N (Si$R^{14}R^{15}R^{16}$)$_2$]—. $R^{14}$, $R^{15}$ and $R^{16}$ are each independently selected from hydrogen, halogen, $C_1$–$C_{20}$ alkyl groups, $C_6$–$C_{30}$ aryl groups, $C_1$–$C_{20}$ alkoxy groups, $C_2$–$C_{20}$ alkenyl groups, $C_7$–$C_{40}$ arylalkyl groups, $C_8$–$C_{40}$ arylalkenyl groups and $C_7$–$C_{40}$ alkylaryl groups, or $R^{14}$ and $R^{15}$, together with the atom(s) connecting them, form a ring; and $M^3$ is selected from carbon, silicon, germanium and tin. Alternatively, $R^{13}$ is represented by the formula:

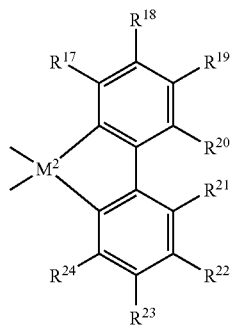

wherein $R^{17}$ to $R^{24}$ are as defined for $R^1$ and $R^2$, or two or more adjacent radicals $R^{17}$ to $R^{24}$, including $R^{20}$ and $R^{21}$, together with the atoms connecting them form one or more rings; $M^2$ is carbon, silicon, germanium, or tin.

$R^8$, $R^9$, $R^{10}$, $R^{11}$ and $R^{12}$ are identical or different and have the meanings stated for $R^4$ to $R^7$.

Additional compounds are suitable as olefin polymerization catalysts for use in this invention. These will be any of those Group-3–10 compounds that can be converted by ligand abstraction or bond scission into a cationic catalyst and stabilized in that state by a noncoordinating or weakly coordinating anion. That anion should be sufficiently labile to be displaced by an olefinically unsaturated monomer such as ethylene.

Exemplary compounds include those described in the patent literature. International patent publications WO 96/23010, WO 97/48735 and Gibson, et al., *Chem. Comm.*, pp. 849–850 (1998), which disclose diimine-based ligands for Group-8 to -10 compounds that undergo ionic activation and polymerize olefins. Polymerization catalyst systems from Group-5–10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5–10, organometallic catalysts of U.S. Pat. No. 6,294,495. Group-11 catalyst precursor compounds, activable with ionizing cocatalysts, useful for olefin and vinylic polar molecules are described in WO 99/30822.

U.S. Pat. No. 5,318,935 describes bridged and unbridged, bisamido catalyst compounds of Group-4 metals capable of α-olefins polymerization. Bridged bis(arylamido) Group-4 compounds for olefin polymerization are described by D. H. McConville, et al., in *Organometallics* 1995, 14, 5478–5480. This reference presents synthetic methods and compound characterizations. Further work appearing in D. H. McConville, et al, *Macromolecules* 1996, 29, 5241–5243, describes bridged bis(arylamido) Group-4 compounds that are polymerization catalysts for 1-hexene. Additional invention-suitable transition metal compounds include those described in WO 96/40805. Cationic Group-3- or Lanthanide-metal olefin polymerization complexes are disclosed in copending U.S. application Ser. No. 09/408,050, filed 29 Sep. 1999. A monoanionic bidentate ligand and two monoanionic ligands stabilize those catalyst precursors, which can be activated with this invention's ionic cocatalysts.

The literature describes many additional suitable catalyst-precursor compounds. Compounds that contain abstractable ligands or that can be alkylated to contain abstractable ligands suit this invention. See, for instance, V. C. Gibson, et al; "The Search for New-Generation Olefin Polymerization Catalysts: Life Beyond Metallocenes", *Angew. Chem. Int. Ed.*, 38, 428–447 (1999).

When using the above catalysts, the catalyst system will generally employ one or more scavenging agents to remove polar impurities from the reaction environment and to increase catalyst activity. Any polymerization reaction components, particularly solvents, monomers, and catalyst feedstreams, can inadvertently introduce impurities and adversely affect catalyst activity and stability. Impurities decrease or even eliminate catalytic activity, particularly with ionizing-anion-activated catalyst systems. Polar impurities, or catalyst poisons, include water, oxygen, metal impurities, etc. These impurities can be removed from or reduced in the reaction components before their addition to the reaction vessel. Impurities can be removed by chemically treating the components or by impurity separation steps. Such treatment or separation can occur during or after synthesis of the components. In any case, the polymerization process will normally employ minor amounts of scavenging agent. Typically, these scavengers will be organometallic such as the Group-13 compounds of U.S. Pat. Nos. 5,153, 157, 5,241,025 and WO-A-91/09882, WO-A-94/03506, WO-A-93/14132, and that of WO 95/0794.1. Exemplary compounds include triethylaluminum, triethylborane, triisobutylaluminum, methylalumoxane, and isobutylalumoxane. Those compounds having bulky or $C_6$–$C_{20}$ linear hydrocarbyl substituents connected to the metal or metalloid center are useful they only weakly coordinate to the active catalyst. Examples include triethylaluminum and bulky compounds such as triisobutylaluminum, triisoprenylaluminum, and long-chain, linear-alkyl-substituted aluminum compounds, such as tri-n-hexylaluminum, tri-n-octylaluminum, or tri-n-dodecylaluminum. When alumoxane is used as activator, any excess over that needed to activate the catalyst can scavenge and additional scavengers may be unnecessary. Alumoxanes also may be used as scavengers with other activators, e.g., methylalumoxane and triisobutyl-alumoxane with boron-based activators. The scavenger amount is limited to that amount effective to enhance activity (and with that amount necessary for activation when used in a dual role) since excess amounts poison catalysts.

This invention's catalyst systems can polymerize those unsaturated molecules conventionally recognized as polymerizable using metallocenes. Typical conditions include solution, slurry, gas-phase, and high-pressure polymerization. The catalysts may be supported on inorganic oxide or polymeric supports and as such will be particularly useful in those operating modes employing fixed-bed, moving-bed, fluid-bed, slurry, or solution processes conducted in single, series, or parallel reactors. WO 98/55518, describes a support method for gas-phase or slurry polymerization. Invention cocatalysts may also function in catalyst prepolymerization.

Alternative polymerization embodiments employ the catalyst system in liquid phase (solution, slurry, suspension, bulk phase, or combinations thereof), in high-pressure liquid or supercritical fluid phase, or in gas phase. These processes may also be employed in singular, parallel, or series reactors. The liquid processes comprise contacting olefin molecules with the catalyst system described above in a suitable diluent or solvent and allowing those molecules to react long enough to produce the invention polymers. (The term polymer encompasses both homo- and co-polymers.) Both aliphatic and aromatic hydrocarbyl solvents are suitable: e.g., hexane. In bulk and slurry processes, the supported catalysts typically contact a liquid monomer slurry. Gas-phase processes use a supported catalyst and use any suitable ethylene polymerization process. Illustrative examples may be found in U.S. Pat. Nos. 4,543,399, 4,588,790, 5,028,670, 5,382,638, 5,352,749, 5,408,017, 5,436,304, 5,453,471, and 5,463,999, 5,767,208 and WO 95/07942.

The minimum reaction temperature is 40° C., although some embodiments select the minimum temperature to be 60° C. The temperature can go as high as 250° C., but some embodiments use temperatures of up to 220° C. The minimum reaction pressure is 0.001 bar. But some embodiments choose minimum pressures of 0.1 bar or 1.0 bar. The maximum pressure is less than or equal to 2500 bar. Some embodiments select the maximum pressure to be 1600 other embodiments select the maximum pressure to be 500 bar.

High-molecular-weight, low-crystallinity, ethylene-α-olefin elastomers (including ethylene-cyclic-olefin and ethylene-α-olefin-diolefin elastomers) can be prepared using catalysts activated by invention activators under traditional solution processes or by introducing ethylene into invention catalyst slurries with α-olefin, cyclic olefin, or either or both mixed with other polymerizable and non-polymerizable diluents. Typical ethylene pressures range from 10 to 1000 psig (69–6895 kPa) and the diluent temperature typically remains between 40 and 160° C. The process can occur in one or more stirred tank reactors, operated individually, in series, or in parallel. The disclosure of U.S. Pat. No. 5,001, 205 illustrates general process conditions. See also, International Application WO 96/33227 and WO 97/22639.

Besides those specifically described above, other molecules may be polymerized using catalysts precursors activated by invention activators. Some examples of these include styrene, alkyl-substituted styrenes, isobutylene and other geminally disubstituted olefins, ethylidene norbornene, norbornadiene, dicyclopentadiene, and other olefinically unsaturated molecules, including other cyclic olefins, such as cyclopentene, norbornene, alkyl-substituted norbornenes, and vinylic polar, polymerizable molecules. See, for example, U.S. Pat. Nos. 5,635,573, 5,763,556, and WO 99/30822. Additionally, α-olefin macromers of 1 to greater than 1000 macromer units may be copolymerized yielding branched olefin polymers. Additionally, activated catalysts for oligomerization, dimerization, hydrogenation, olefin/carbon-monoxide copolymerization, hydroformulation, hydrosilation, hydroamination, and related reactions can be activated with invention cocatalysts.

The invention cocatalysts can activate individual catalysts or can activate catalyst mixtures for polymer blends. Adept monomer and catalyst selection yields polymer blends analogous to those using individual catalyst compositions. Polymers having increased MWD (for improved processing) and other benefits available from mixed-catalyst-system polymers can be achieved using invention cocatalysts.

Blended polymer formation can be achieved ex situ through mechanical blending or in situ through using mixed catalyst systems. It is generally believed that in situ blending provides a more homogeneous product and allows one-step blend production. In-situ blending with mixed catalyst systems involves combining more than one catalyst in the same reactor to simultaneously produce multiple, distinct polymer products. This method requires additional catalyst synthesis, and the various catalyst components must be matched for their activities, the polymer products they generate at specific conditions, and their response to changes in polymerization conditions. Invention cocatalysts can activate mixed catalyst systems.

Invention catalyst systems can produce a variety of polyethylene types including high- and ultra-high-molecular weight polyethylenes. These polyethylenes can be either homopolymers or copolymers with other α-olefins or α-olefinic or non-conjugated diolefins, e.g. $C_3$–$C_{20}$ olefins, diolefins, or cyclic olefins. In some embodiments, a low-pressure (typically <50 bar) vessel is used. Invention activated catalysts are slurried with a solvent (typically hexane or toluene). The polyethylenes are produced by adding ethylene, and optionally one or more other monomers, along with the slurried catalyst to the low-pressure vessel. The temperature is usually within the 40–250° C. range. Cooling removes polymerization heat. Gas-phase polymerization can be conducted, for example, in a continuous fluid-bed, gas-phase reactor operated at a minimum of 2000 kPa and up to 3000 kPa. The minimum temperature is 60° C.; the maximum temperature is 160° C. Some gas-phase reaction embodiments uses hydrogen as a reaction modifier at a concentration of no less than 100 PPM. The hydrogen gas concentration should not exceed 200 PPM. The reaction employs a $C_4$–$C_8$ comonomer feedstream and a $C_2$ feedstream. The $C_4$–$C_8$ feedstream goes down to 0.5 mol %. It also may go up to 1.2 mol %. Finally, the $C_2$ feedstream has a minimum concentration of 25 mol %. Its maximum concentration is 35 mol %. See, U.S. Pat. Nos. 4,543,399, 4,588,790, 5,028,670 and 5,405,922 and 5,462,999.

Exemplary Catalyst Precursor Embodiments That are within the Scope of This Invention dimethylsilyl bis(cyclopentadienyl)hafnium dihydride; pentamethylcyclopentadienyltitanium isopropoxide; (benzylcyclopentadienyl)(cyclopentadienyl)hafnium dihydride; (benzylcyclopentadienyl)(cyclopentadienyl)hafnium dimethyl; (benzylcyclopentadienyl)(cyclopentadienyl)titanium dihydride; (benzylcyclopentadienyl)(cyclopentadienyl)titanium dimethyl; (benzylcyclopentadienyl)(cyclopentadienyl)zirconium dihydride; (benzylcyclopentadienyl)(cyclopentadienyl)zirconium dimethyl; (cyclohexylmethylcyclopentadienyl)(cyclopentadienyl)hafnium dihydride; (cyclohexylmethylcyclopentadienyl)(cyclopentadienyl)hafnium dimethyl; (cyclohexylmethylcyclopentadienyl)(cyclopentadienyl)titanium dihydride; (cyclohexylmethylcyclopentadienyl)(cyclopentadienyl)titanium dimethyl; (cyclohexylmethylcyclopentadienyl)(cyclopentadienyl)zirconium dihydride; (cyclohexylmethylcyclopentadienyl)(cyclopentadienyl)zirconium dimethyl; (cyclopentadienyl)zirconium tribenzyl; (cyclopentadienyl)zirconium trimethyl; (cyclopentadienyl)zirconium triphenyl; (dimethylcyclopentadienyl)(cyclopentadienyl)hafnium dihydride; (dimethylcyclopentadienyl)(cyclopentadienyl)hafnium dimethyl; (dimethylcyclopentadienyl)(cyclopentadienyl)titanium dihydride; (dimethylcyclopentadienyl)(cyclopentadienyl)titanium dimethyl; (dimethylcyclopentadienyl)(cyclopentadienyl)zirconium dihydride; (dimethylcyclopentadienyl)(cyclopentadienyl)zirconium dimethyl; (dimethylcyclopentadienyl)zirconium trimethyl; (diphenylmethylcyclopentadienyl)(cyclopentadienyl)hafnium dihydride; (diphenylmethylcyclopentadienyl)(cyclopentadienyl)hafnium dimethyl; (diphenylmethylcyclopentadienyl)(cyclopentadienyl)titanium dihydride; (diphenylmethylcyclopentadienyl)(cyclopentadienyl)titanium dimethyl; (diphenylmethylcyclopentadienyl)(cyclopentadienyl)zirconium dihydride; (diphenylmethylcyclopentadienyl)(cyclopentadienyl)zirconium dimethyl; (ethylcyclopentadienyl)(cyclopentadienyl)hafnium dihydride; (ethylecyclpentadienyl)(cyclopentadienyl)hafnium dimethyl; (ethylcyclopentadienyl)(cyclopentadienyl)titanium dihydride; (ethylcyclopentadienyl)(cyclopentadienyl)titanium dimethyl; (ethylcyclopentadienyl)(cyclopentadienyl)zirconium dihydride; (ethylcyclopentadienyl)(cyclopentadienyl)zirconium dimethyl; (ethyltetramethylcyclopentadienyl)(cyclopentadienyl)hafnium dihydride; (ethyltetramethylcyclopentadienyl)(cyclopentadienyl)hafnium dimethyl; (ethyltetramethylcyclopentadienyl)(cyclopentadienyl)titanium dihydride; (ethyltetramethylcyclopentadienyl)(cyclopentadienyl)titanium dimethyl; (ethyltetramethylcyclopentadienyl)(cyclopentadienyl)zirconium dihydride; (ethyltetramethylcyclopentadienyl)(cyclopentadienyl)zirconium dimethyl; (indenyl)(cyclopentadienyl)hafnium dihydride; (indenyl)(cyclopentadienyl)hafnium dimethyl; (indenyl)(cyclopentadienyl)titanium dihydride; (indenyl)(cyclopentadienyl)titanium dimethyl; (indenyl)(cyclopentadienyl)zirconium dihydride; (indenyl)(cyclopentadienyl)zirconium dimethyl; (methylcyclopentadienyl)(cyclopentadienyl)hafnium dihydride; (methylcyclopentadienyl)(cyclopentadienyl)hafnium dimethyl; (methylcyclopentadienyl)(cyclopentadienyl)titanium dihydride; (methylcyclopentadienyl)(cyclopentadienyl)titanium dimethyl; (methylcyclopentadienyl)(cyclopentadienyl)zirconium dihydride; (methylcyclopentadienyl)(cyclopentadienyl)zirconium dimethyl; (methylcyclopentadienyl)zirconium tribenzyl; (methylcyclopentadienyl)zirconium trimethyl; (methylcyclopentadienyl)zirconium triphenyl; (butylcyclopentadienyl)(cyclopentadienyl)hafnium dihydride; (butylcyclopentadienyl)(cyclopentadienyl)hafnium dimethyl; (butylcyclopentadienyl)(cyclopentadienyl)titanium dihydride; (nbutylcyclopentadienyl)(cyclopentadienyl)titanium dimethyl; (nbutylcyclopentadienyl)(cyclopentadienyl)zirconium dihydride; (nbutylcyclopentadienyl)(cyclopentadienyl)zirconium dimethyl; (pentamethylcyclopentadienyl)(cyclopentadienyl)hafnium dihydride; (pentamethylcyclopentadienyl)(cyclopentadienyl)hafnium dimethyl; (pentamethylcyclopentadienyl)(cyclopentadienyl)titanium dihydride; (pentamethylcyclopentadienyl)(cyclopentadienyl)titanium dimethyl; (pentamethylcyclopentadienyl)(cyclopentadienyl)zirconium dihydride; (pentamethylcyclopentadienyl)(cyclopentadienyl)zirconium dimethyl; (pentamethylcyclopentadienyl)scandium bis(bistrimethylsilylmethyl); (pentamethylcyclopentadienyl)yttrium bis(bistrimethylsilylmethyl); (pentamethylcyclopentadienyl)zirconium tribenzyl; (pentamethylcyclopentadienyl)zirconium trimethyl; (pentamethylcyclopentadienyl)zirconium triphenyl; (pentamethylcyclopentadienylcyclopentadienyl)zirconium dimethyl; (propylcyclopentadienyl)(cyclopentadienyl)hafnium dihydride; (propylcyclopentadienyl)(cyclopentadienyl)hafnium dimethyl; (propylcyclopentadienyl)(cyclopentadienyl)titanium dihydride; (propylcyclopentadienyl)(cyclopentadienyl)titanium dimethyl; (propylcyclopentadienyl)(cyclopentadienyl)zirconium dihydride; (propylcyclopentadienyl)(cyclopentadienyl)zirconium dimethyl; (t-butylcyclopentadienyl)(cyclopentadienyl)hafnium dihydride; (t-butylcyclopentadienyl)(cyclopentadienyl)hafnium dimethyl; (t-butylcyclopentadienyl)(cyclopentadienyl)titanium dihydride; (t-butylcyclopentadienyl)(cyclopentadienyl)titanium dimethyl; (t-butylcyclopentadienyl)(cyclopentadienyl)zirconium dihydride; (t-butylcyclopentadienyl)(cyclopentadienyl)zirconium dimethyl; (tetramethylcyclopentadienyl)(cyclopentadienyl)hafnium dihydride; (tetramethylcyclopentadienyl)(cyclopentadienyl)hafnium dimethyl; (tetramethylcyclopentadienyl)(cyclopentadienyl)titanium dihydride; (tetramethylcyclopentadienyl)(cyclopentadienyl)titanium dimethyl; (tetramethylcyclopentadienyl)(cyclopentadienyl)zirconium dihydride; (tetramethylcyclopentadienyl)(cyclopentadienyl)zirconium dimethyl; (tetramethylcyclopentadienyl)(npropylcyclopentadienyl)zirconium dimethyl; (tetramethylcyclopentadienyl)zirconium trimethyl; (trifluoromethylcyclopentadienyl)(cyclopentadienyl)hafnium dihydride; (trifluoromethylcyclopentadienyl)(cyclopentadienyl)hafnium dimethyl; (trifluoromethylcyclopentadienyl)(cyclopentadienyl)titanium dihydride; (trifluoromethylcyclopentadienyl)(cyclopentadienyl)titanium dimethyl; (trifluoromethylcyclopentadienyl)(cyclopentadienyl)zirconium dihydride; (trifluoromethylcyclopentadienyl)(cyclopentadienyl)zirconium dimethyl; (trimethylcyclopentadienyl)(cyclopentadienyl)hafnium dihydride; (trimethylcyclopentadienyl)(cyclopentadienyl)hafnium dimethyl; (trimethylcyclopentadienyl)(cyclopentadienyl)titanium dihydride; (trimethylcyclopentadienyl)(cyclopentadienyl)titanium dimethyl; (trimethylcyclopentadienyl)(cyclopentadienyl)zirconium dihydride; (trimethylcyclopentadienyl)(cyclopentadienyl)zirconium dimethyl; (trimethylcyclopentadienyl)zirconium trimethyl; (trimethylgermylcyclopentadienyl)(cyclopentadienyl)hafnium dihydride; (trimethylgermylcyclopentadienyl)(cyclopentadienyl)hafnium dimethyl; (trimethylgermylcyclopentadienyl)(cyclopentadienyl)titanium dihydride;

(trimethylgermylcyclopentadienyl)(cyclopentadienyl)titanium dimethyl; (trimethylgermylcyclopentadienyl)(cyclopentadienyl)zirconium dihydride; (trimethylgermylcyclopentadienyl)(cyclopentadienyl)zirconium dimethyl; (trimethylplumbyl cyclopentadienyl)(cyclopentadienyl)zirconium dimethyl; (trimethylplumbylcyclopentadienyl)(cyclopentadienyl)hafnium dihydride; (trimethylplumbylcyclopentadienyl)(cyclopentadienyl)hafnium dimethyl; (trimethylplumbylcyclopentadienyl)(cyclopentadienyl)titanium dihydride; (trimethylplumbylcyclopentadienyl)(cyclopentadienyl)titanium dimethyl; (trimethylplumbylcyclopentadienyl)(cyclopentadienyl)zirconium dihydride; (trimethylsilylcyclopentadienyl)(cyclopentadienyl)hafnium dihydride; (trimethylsilylcyclopentadienyl)(cyclopentadienyl)hafnium dimethyl; (trimethylsilylcyclopentadienyl)(cyclopentadienyl)titanium dihydride; (trimethylsilylcyclopentadienyl)(cyclopentadienyl)titanium dimethyl; (trimethylsilylcyclopentadienyl)(cyclopentadienyl)zirconium dihydride; (trimethylsilylcyclopentadienyl)(cyclopentadienyl)zirconium dimethyl; (trimethylsilylcyclopentadienyl)zirconium trimethyl; (trimethylstannylcyclopentadienyl)(cyclopentadienyl)hafnium dihydride; (trimethylstannylcyclopentadienyl)(cyclopentadienyl)titanium dihydride; (trimethylstannylcyclopentadienyl)(cyclopentadienyl)zirconium dihydride; [(4-nbutylphenyl)(4-t-butylphenyl)methylene](cyclopentadienyl)(fluorenyl)hafnium dimethyl; [1,1'(1,1,2,2-tetramethyldisilanylene)bis(3-methylcyclopentadienyl)]zirconium dimethyl; [1,1'(1,1,2,2-tetramethyldisilanylene)bis(3-trimethylsilanylcyclopentadienyl)]zirconium dimethyl; [1,1'(1,1,2,2-tetramethyldisilanylene)bis(4,5,6,7-tetrahydroindenyl)]hafnium dimethyl; [1,1'(1,1,2,2-tetramethyldisilanylene)bis(4,5,6,7-tetrahydroindenyl)]titanium dimethyl; [1,1'(1,1,2,2-tetramethyldisilanylene)bis(4,5,6,7-tetrahydroindenyl)]zirconium dimethyl; [1,1'(1,1,3,3-tetramethyldisiloxanylene)bis(4,5,6,7-tetrahydroindenyl)]hafnium dimethyl; [1,1'(1,1,3,3-tetramethyldisiloxanylene)bis(4,5,6,7-tetrahydroindenyl)]titanium dimethyl; [1,1'(1,1,3,3-tetramethyldisiloxanylene)bis(4,5,6,7-tetrahydroindenyl)]zirconium dimethyl; [1,1'(1,1,4,4-tetramethyl-1,4-disilanylbutylene)bis(4,5,6,7-tetrahydroindenyl)]hafnium dimethyl; [1,1'(1,1,4,4-tetramethyl-1,4-disilanylbutylene)bis(4,5,6,7-tetrahydroindenyl)]titanium dimethyl; [1,1'(1,1,4,4-tetramethyl-1,4-disilanylbutylene)bis(4,5,6,7-tetrahydroindenyl)]titanium dimethyl; [1,1'(1,1,4,4-tetramethyl-1,4-disilanylbutylene)bis(4,5,6,7-tetrahydroindenyl)]zirconium dimethyl; [1,1 '(2,2-dimethyl-2-silapropylene)bis(3-methylcyclopentadienyl)]hafnium dimethyl; [1,1'(2,2-dimethyl-2-silapropylene)bis(3-methylcyclopentadienyl)]titanium dimethyl; [1,1'(2,2-dimethyl-2-silapropylene)bis(3-methylcyclopentadienyl)]zirconium dimethyl; [1,1'dimethylsilanylenebis(2-methy-4-naphth-2-yl-lindenyl)]hafnium dimethyl; [1,1'dimethylsilanylenebis(2-methy-4-phenyl-lindenyl)]hafnium dimethyl; [1,1'dimethylsilanylenebis(2-methylindenyl)]hafnium dimethyl; [1,1'dimethylsilanylenebis(3-methylcyclopentadienyl)]hafnium dimethyl; [1,1'dimethylsilanylenebis(3-methylcyclopentadienyl)]titanium dimethyl; [1,1'dimethylsilanylenebis(3-methylcyclopentadienyl)]zirconium dimethyl; [1,1'dimethylsilanylenebis(3-trimethylsilanylcyclopentadienyl)]hafnium dimethyl; [1,1'dimethylsilanylenebis(3-trimethylsilanylcyclopentadienyl)]titanium dimethyl; [1,1'dimethylsilanylenebis(3-trimethylsilanylcyclopentadienyl)]zirconium dimethyl; [1,1'dimethylsilanylenebis(4,5,6,7-tetrahydroindenyl)]hafnium dimethyl; [1,1'dimethylsilanylenebis(4,5,6,7-tetrahydroindenyl)]titanium dimethyl; [1,1'dimethylsilanylenebis(4,5,6,7-tetrahydroindenyl)]zirconium dimethyl; [1,1'dimethylsilanylenebis(indenyl)]hafnium dimethyl; [1,1'dimethylsilanylenebis(indenyl)]titanium dimethyl; [1,1'dimethylsilanylenebis(indenyl)]zirconium dimethyl; 3-butylcyclopentadienyl)zirconium dimethyl; and fluorenyl-ligandcontaining compounds; bis(2,5-di-t-butylphenoxy)zirconium dimethyl; bis(4-[triethylsilyl])methylene (cyclopentadienyl)(2,7-di-t-butylfluorenyl)hafnium dimethyl.; bis(4-[triethylsilyl])methylene (cyclopentadienyl)(fluorenyl)hafnium dimethyl; bis(benzylcyclopentadienyl)hafnium dihydride; bis(benzylcyclopentadienyl)hafnium dimethyl; bis(benzylcyclopentadienyl)titanium dihydride; bis(benzylcyclopentadienyl)titanium dimethyl; bis(benzylcyclopentadienyl)zirconium dihydride; bis(benzylcyclopentadienyl)zirconium dimethyl; bis(cyclohexylmethylcyclopentadienyl)hafnium dihydride; bis(cyclohexylmethylcyclopentadienyl)hafnium dimethyl; bis(cyclohexylmethylcyclopentadienyl)titanium dihydride; bis(cyclohexylmethylcyclopentadienyl)titanium dimethyl; bis(cyclohexylmethylcyclopentadienyl)zirconium dihydride; bis(cyclohexylmethylcyclopentadienyl)zirconium dimethyl; bis(cyclopentadienyl)(trimethylsilyl)(benzyl)zirconium; bis(cyclopentadienyl)(trimethylsilyl)(methyl)hafnium; bis(cyclopentadienyl)(trimethylsilyl)(methyl)titanium; bis(cyclopentadienyl)(trimethylsilyl)(methyl)zirconium; bis(cyclopentadienyl)(trimethylsilyl)(trimethylsilyl methyl)zirconium; bis(cyclopentadienyl)(trimethylsilyl)(tris(trimethylsilyl)(trimethylsilyl-benzyl); bis(cyclopentadienyl)(triphenylsilyl)(methyl)hafnium; bis(cyclopentadienyl)(triphenylsilyl)(methyl)titanium; bis(cyclopentadienyl)(triphenylsilyl)(methyl)zirconium; bis(cyclopentadienyl)[bis(methylsilyl)silyl](methyl)zirconium; bis(cyclopentadienyl)[tris(dimethylsilyl)silyl](methyl)hafnium; bis(cyclopentadienyl)[tris(dimethylsilyl)silyl](methyl)titanium; bis(cyclopentadienyl)[tris(dimethylsilyl)silyl](methyl)zirconium; bis(cyclopentadienyl)hafnium di(mtolyl); bis(cyclopentadienyl)hafnium di(ptolyl); bis(cyclopentadienyl)hafnium dibutyl; bis(cyclopentadienyl)hafnium diethyl; bis(cyclopentadienyl)hafnium dihydride; bis(cyclopentadienyl)hafnium dimethyl; bis(cyclopentadienyl)hafnium dineopentyl; bis(cyclopentadienyl)hafnium diphenyl; bis(cyclopentadienyl)hafnium dipropyl; bis(cyclopentadienyl)titanium di(mtolyl); bis(cyclopentadienyl)titanium di(ptolyl); bis(cyclopentadienyl)titanium dibutyl; bis(cyclopentadienyl)titanium diethyl; bis(cyclopentadienyl)titanium dihydride; bis(cyclopentadienyl)titanium dimethyl; bis(cyclopentadienyl)titanium dineopentyl; bis(cyclopentadienyl)titanium diphenyl; bis(cyclopentadienyl)titanium dipropyl; bis(cyclopentadienyl)zirconium di(mtolyl); bis(cyclopentadienyl)zirconium di(ptolyl); bis(cyclopentadienyl)zirconium dibenzyl; bis(cyclopentadienyl)zirconium dibutyl; bis(cyclopentadienyl)zirconium dichlorohydride; bis(cyclopentadienyl)zirconium diethyl; bis(cyclopentadienyl)zirconium dihydride; bis(cyclopentadienyl)zirconium dimethyl; bis(cyclopentadienyl)zirconium dineopentyl; bis(cyclopentadienyl)zirconium diphenyl; bis(cyclopentadienyl)zirconium dipropyl; bis(dimethylcyclopentadienyl)hafnium dihydride; bis(dimethylcyclopentadienyl)hafnium dimethyl; bis(dimethylcyclopentadienyl)titanium dihydride; bis(dimethylcyclopentadienyl)titanium dimethyl; bis(dimethylcyclopentadienyl)zirconium dihydride; bis(dimethylcyclopentadienyl)zirconium dimethyl; bis(diphenylmethylcyclopentadienyl)hafnium dihydride; bis(diphenylmethylcyclopentadienyl)hafnium dimethyl; bis(diphenylmethylcyclopentadienyl)titanium dihydride; bis(diphenylmethylcyclopentadienyl)titanium dimethyl, bis (diphenylmethylcyclopentadienyl)zirconium dihydride; bis(diphenylmethylcyclopentadienyl)zirconium dimethyl; bis(ethylcyclopentadienyl)hafnium dimethyl; bis(ethylcyclopentadienyl)titanium dimethyl; bis(ethylcyclopentadienyl)zirconium dihydride; bis(ethylcyclopentadienyl)zirconium dimethyl; bis(ethyltetramethylcyclopentadienyl)hafnium dihydride; bis(ethyltetramethylcyclopentadienyl)hafnium dimethyl; bis(ethyltetramethylcyclopentadienyl)titanium dihydride; bis(ethyltetramethylcyclopentadienyl)titanium dimethyl; bis(ethyltetramethylcyclopentadienyl)zirconium dihydride; bis(ethyltetramethylcyclopentadienyl)zirconium dimethyl; bis(hexamethyldisilazido)dimethyltitanium; bis(indenyl)hafnium dihydride; bis(indenyl)hafnium dimethyl; bis(indenyl)titanium dihydride; bis(indenyl)titanium dimethyl; bis(indenyl)zirconium dihydride; bis(indenyl)zirconium dimethyl; bis(methycyclopentadienyl)zirconium dibenzyl; bis(methylcyclopentadienyl)hafnium dihydride; bis(methylcyclopentadienyl)hafnium dimethyl; bis(methylcyclopentadienyl)titanium dihydride; bis(methylcyclopentadienyl)titanium dimethyl; bis(methylcyclopentadienyl)zirconium dibenzyl; bis(methylcyclopentadienyl)zirconium dihydride; bis(methylcyclopentadienyl)zirconium dimethyl; bis(methylcyclopentadienyl)zirconium diphenyl; bis(nbutylcyclopentadienyl)hafnium dihydride; bis(nbutylcyclopentadienyl)hafnium dimethyl; bis(nbutylcyclopentadienyl)titanium dihydride; bis(nbutylcyclopentadienyl)titanium dimethyl; bis(nbutylcyclopentadienyl)zirconium dihydride; bis(nbutylcyclopentadienyl)zirconium dimethyl; bis(pentamethylcyclopentadienyl)(benzyne)hafnium; bis(pentamethylcyclopentadienyl)(benzyne)titanium; bis(pentamethylcyclopentadienyl)(benzyne)zirconium; bis(pentamethylcyclopentadienyl)hafnium (methyl)(hydride); bis(pentamethylcyclopentadienyl)hafnium (phenyl)(hydride); bis(pentamethylcyclopentadienyl)hafnium dihydride; bis(pentamethylcyclopentadienyl)hafnium dimethyl; bis(pentamethylcyclopentadienyl)titanium (methyl)(hydride); bis(pentamethylcyclopentadienyl)titanium (phenyl)(hydride); bis(pentamethylcyclopentadienyl)titanium dihydride; bis(pentamethylcyclopentadienyl)titanium dimethyl; bis(pentamethylcyclopentadienyl)zirconacyclobutane; bis(pentamethylcyclopentadienyl)zirconacyclopentane; bis(pentamethylcyclopentadienyl)zirconium (methyl)(hydride); bis(pentamethylcyclopentadienyl)zirconium (phenyl)(hydride); bis(pentamethylcylopentadienyl)zirconium dibenzyl; bis(pentamethylcyclopentadienyl)zirconium dihydride; bis(pentamethylcyclopentadienyl)zirconium dimethyl; bis(pentamethylcyclopentadienyl)zirconium methylhydride; bis(pentamethylcyclopentadienyl)zirconium methylmethyl; bis(propylcyclopentadienyl)hafnium dihydride; bis(propylcyclopentadienyl)hafnium dimethyl; bis(propylcyclopentadienyl)titanium dihydride; bis(propylcyclopentadienyl)titanium dimethyl; bis(propylcyclopentadienyl)zirconium dihydride; bis(propylcyclopentadienyl)zirconium dimethyl; bis(t-butylcyclopentadienyl)hafnium dihydride; bis(t-butylcyclopentadienyl)hafnium dimethyl; bis(t-butylcyclopentadienyl)titanium dihydride; bis(t-butylcyclopentadienyl)titanium dimethyl; bis(t-butylcyclopentadienyl)zirconium dihydride; bis(t-butylcyclopentadienyl)zirconium dimethyl; bis(tetramethylcyclopentadienyl)hafnium dihydride; bis(tetramethylcyclopentadienyl)hafnium dimethyl; bis(tetramethylcyclopentadienyl)titanium dihydride; bis(tetramethylcyclopentadienyl)titanium dimethyl; bis(tetramethylcyclopentadienyl)zirconium dihydride; bis(tetramethylcyclopentadienyl)zirconium dimethyl; bis(trifluoromethylcyclopentadienyl)hafnium dihydride; bis(trifluoromethylcyclopentadienyl)hafnium dimethyl; bis(trifluoromethylcyclopentadienyl)titanium dihydride; bis(trifluoromethylcyclopentadienyl)titanium dimethyl; bis(trifluoromethylcyclopentadienyl)zirconium dihydride; bis(trifluoromethylcyclopentadienyl)zirconium dimethyl; bis(trimethylcyclopentadienyl)hafnium dihydride; bis(trimethylcyclopentadienyl)hafnium dimethyl; bis(trimethylcyclopentadienyl)titanium dihydride; bis(trimethylcyclopentadienyl)titanium dimethyl; bis(trimethylcyclopentadienyl)zirconium dihydride; bis(trimethylcyclopentadienyl)zirconium dimethyl; bis(trimethylgermylcyclopentadienyl)hafnium dihydride; bis(trimethylgermylcyclopentadienyl)hafnium dimethyl; bis(trimethylgermylcyclopentadienyl)titanium dihydride; bis(trimethylgermylcyclopentadienyl)titanium dimethyl; bis(trimethylgermylcyclopentadienyl)zirconium dihydride; bis(trimethylgermylcyclopentadienyl)zirconium dimethyl; bis(trimethylplumbylcyclopentadienyl)hafnium dihydride; bis(trimethylplumbylcyclopentadienyl)hafnium dimethyl; bis(trimethylplumbylcyclopentadienyl)titanium dihydride; bis(trimethylplumbylcyclopentadienyl)titanium dimethyl; bis(trimethylplumbylcyclopentadienyl)zirconium dihydride; bis(trimethhylplumbylcyclopentadienyl)zirconium dimethyl; bis(trimethylsilylcyclopentadienyl)hafnium dihydride; bis(trimethylsilylcyclopentadienyl)hafnium dimethyl; bis(trimethylsilylcyclopentadienyl)titanium dihydride; bis(trimethylsilylcyclopentadienyl)titanium dimethyl; bis(trimethylsilylcyclopentadienyl)zirconium dihydride; bis(trimethylsilylcyclopentadienyl)zirconium dimethyl; bis(trimethylstannylcyclopentadienyl)hafnium dihydride; bis(trimethylstannylcyclopentadienyl)titanium dihydride; bis(trimethylstannylcyclopentadienyl)zirconium dihydride; bridged biscyclopentadienyl; cyclobutylidene(cyclopentadienyl)(9-fluorenyl)zirconium dimethyl; cyclohyxylidene(cyclopentadienyl)(9-fluorenyl)zirconium dimethyl; cyclopentadienylchromium 2,4-pentadienyl; cyclopentadienylscandium bis(ptolyl); cyclopentadienyltitanium trimethyl; cyclopentadienyltitanium triphenyl; cyclopentadienylzirconium triethyl; cyclopentadienylzirconium trimethyl; cyclopentadienylzirconium tripropyl; cyclopentylidene(cyclopentadienyl)(9-fluorenyl)zirconium dimethyl; dibutylsilyl (fluorenyl)(cyclopentadienyl)hafnium dimethyl; diethylsilanediylbis(2-methylindenyl)zirconium diethyl; diethylsilanediylbis(2-methylindenyl)zirconium dimethyl; dimethylcyclopentadienyl(cyclopentadienyl)zirconium dihydride; dimethylcyclopentadienyl(cyclopentadienyl)zirconium dimethyl; dimethylsilanediylbis(2-ethyl-5-isopropylcyclopentadienyl)zirconium dimethyl; dimethylsilanediylbis(2-ethylindenyl)zirconium dimethyl; dimethylsilanediylbis(2-isopropylindenyl)zirconium dimethyl; dimethylsilanediylbis(2-methyl-5-ethylcyclopentadienyl)zirconium dimethyl; dimethylsilanediylbis(2-methyl-5-methylcyclopentadienyl)zirconium dimethyl; dimethylsilanediylbis(2-methylbenzindenyl)zirconium dimethyl; dimethylsilanediylbis(2-methylindanyl)zirconium dimethyl; dimethylsilanediylbis(2-methylindenyl)hafnium dimethyl.; dimethylsilanediylbis(2-methylindenyl)zirconium dimethyl; dimethylsilanediylbis(2-t-butylindenyl)zirconium dimethyl; dimethylsilanylene (tetramethylcyclopentadienyl)(nadamantylamido)titanium dimethyl; dimethylsilanylene (tetramethylcyclopentadienyl)(n-t-butylamido)titanium dimethyl; dimethylsily (bisindenyl)zirconium dichloride; dimethylsily(bisindenyl)hafnium dimethyl; dimethylsilyl (bisindenyl)zirconium dichloride; dimethylsilyl (indenyl)(fluorenyl)hafnium dihydride; dimethylsilyl bis (2-methylindenyl)hafnium dimethyl; dimethylsilyl bis(2- propylindenyl)hafnium dimethyl; dimethylsilyl bis(4-methyl, 2-phenylindenyl)hafnium dimethyl; dimethylsilyl bis(cyclopentadienyl)hafnium dihydride; dimethylsilyl bis(cyclopentadienyl)titanium dihydride; dimethylsilyl bis(cyclopentadienyl)zirconium dihydride; dimethylsilyl bis(indenyl)hafnium dimethyl; dimethylsilyl(bisindenyl)hafnium dimethyl; dimethylsilyl(cyclopentadienyl)(fluorenyl)zirconium dimethyl; dimethylsilyl(methylcyclopentadienyl)(1-fluorenyl)hafnium dihydride; dimethylsilyl(methylcyclopentadienyl)(1-fluorenyl)titanium dihydride; dimethylsilyl (methylcyclopentadienyl)(1-fluorenyl)zirconium dihydride; dimethylsilyl(tetramethylclopentadienyl)cyclodecyloamido)titanium dimethyl; dimethylsilyl(tetramethylcyclopentadienyl)(t-butylamido)titanium dimethyl; dimethylsilyl (tetramethyleyclopentadienyl)(1-adamantylamido)titanium dimethyl; dimethylsilylbis(2-methylbenzindenyl)zirconium dichloride; dimethylsilylbis(2-methylbenzindenyl)zirconium dimethyl; dimethylsilylbis(3-trimethylsilylcyclopentadienyl)hafnium dihydride; dimethylsilylbis(3-trimethylsilylcyclopentadienyl)titanium dihydride; dimethylsilylbis(3-trimethylsilylcyclopentadienyl)zirconium dihydride; dimethylsilylbis(cyclopentadienyl)zirconium dihydride.; dimethylsilylbis(cyclopentadienyl)zirconium dimethyl; dimethylsilylbis(indenyl)hafnium dimethyl; dimethylsilylbis(indenyl)titanium dimethyl; dimethylsilylbis(indenyl)zirconium dimethyl; dimethylsilylbis(tetrahydroindenyl)zirconium dichloride; dimethylsilylene(cyclopentadienyl)(9-fluorenyl)zirconium dimethyl; dimethylsilylenebis(2,3,5-trimethylcyclopentadienyl)zirconium dimethyl; dimethylsilylenebis(cyclopentadienyl)zirconium dimethyl; dimethylsilylenebis(indenyl)zirconium dimethyl; dimethylsilyltetramethylcyclopentadienyldodecylamido hafnium dihydride; dimethylsilyltetramethylcyclopentadienyldodecylamido hafnium dimethyl; dimethylsilyltetramethylcyclopentadienyl-t-butylamido titanium dichloride; dimethylsilyltetramethylcyclopentadienyl-t-butylamido zirconium dimethyl; dimethylthiobis(2-methylindenyl)zirconium dimethyl; dinapthylmethylene (cyclopentadienyl)(fluorenyl)hafnium dimethyl; diphenylmethyl (fluorenyl)(cyclopentadienyl)zirconium dimethyl; diphenylmethylene (2,7-dinbutylfluorenyl)(cyclopentadienyl)hafnium dimethyl; diphenylmethylene (2,7-dinbutylfluorenyl)(fluorenyl)hafnium dimethyl; diphenylmethylene (2,7-di-t-butyl-5-methylfluorenyl)(cyclopentadienyl)hafnium dimethyl; diphenylmethylene (2,7-di-t-butylfluorenyl)(cyclopentadienyl)hafnium dimethyl; diphenylmethylene (2,7-di-t-butylfluorenyl)(fluorenyl)hafnium dimethyl; diphenylmethylene (cyclopentadienyl)(2,7-dimethylfluorenyl)hafnium dimethyl; diphenylmethylene (cyclopentadienyl)(2,7-di-t-butylfluorenyl)hafnium dimethyl; diphenylmethylene (cyclopentadienyl)(fluorenyl)hafnium dimethyl; diphenylmethylene (indenyl)(2,7-di-t-butylfluorenyl)hafnium dibenzyl; diphenylmethylene(cyclopentadienyl)(9-fluorenyl)zirconium dimethyl; ethylcyclopentadienyl(cyclopentadienyl)zirconium dihydride; ethylcyclopentadienyl(cyclopentadienyl)zirconium dimethyl; ethylene bis(cyclopentadienyl)hafnium dihydride; ethylene bis(cyclopentadienyl)hafnium dimethyl; ethylene bis(cyclopentadienyl)titanium dihydride; ethylene bis(cyclopentadienyl)titanium dihydride; ethylene bis(cyclopentadienyl)titanium dimethyl; ethylene bis(cyclopentadienyl)zirconium dihydride; ethylene bis(cyclopentadienyl)zirconium dihydride; ethylene bis(cyclopentadienyl)zirconium dimethyl; ethylene(cyclopentadienyl)(9-fluorenyl)zirconium dimethyl; ethylenebis(cyclopentadienyl)zirconium dihydride; ethylenebis(cyclopentadienyl)zirconium dimethyl; ethylenebis(indenyl) hafnium dimethyl; ethylenebis(indenyl)titanium dimethyl; ethylenebis(indenyl)zirconium dimethyl; ethylenebis(tetrahydroindenyl)hafnium dimethyl; ethylenebis(tetrahydroindenyl)titanium dimethyl; ethylenebis(tetrahydroindenyl)zirconium dimethyl; ethyltetramethylcyclopentadienyl(cyclopentadienyl)zirconium dihydride; ethyltetramethylcyclopentadienyl(cyclopentadienyl)zirconium dimethyl; fluorenylzirconium trimethyl; indenyl(cyclopentadienyl)zirconium dihydride; indenyl(cyclopentadienyl)zirconium dimethyl; indenylzirconium trimethyl; ipropyl(cyclopentadienyl)(fluorenyl)hafnium dimethyl; isopropylidene(cyclopentadienyl)(fluorenyl)zirconium dihydride, bis(cyclopentadienyl)zirconium dimethyl; isopropyl(cyclopentadienyl)(1-fluorenyl)hafnium dimethyl; isopropyl(cyclopentadienyl)(1-fluorenyl)titanium dimethyl; isopropyl(cyclopentadienyl)(1-fluorenyl)zirconium dimethyl; isopropyl(cyclopentadienyl)(1-octahydrofluorenyl)hafnium dimethyl; isopropyl(cyclopentadienyl)(1-octahydrofluorenyl)titanium dimethyl; isopropyl(cyclopentadienyl)(1-octahydrofluorenyl)zirconium dimethyl; isopropylidene(cyclopentadienyl)(9-fluorenyl)zirconium dimethyl; isopropylidene(cyclopentadienyl)(fluorenyl)zirconium dihydride, bis(cyclopentadienyl)zirconium dimethyl; isopropylidene(cyclopentadienyl)(fluorenyl)zirconium dimethyl; isopropylidenebis(cyclopentadienyl)zirconium dihydride; isopropylidenebis(cyclopentadienyl)zirconium dihydride; isopropylidenebis(cyclopentadienyl)zirconium dimethyl; isopropylidenebis(indenyl)zirconium dihydride; isopropylidenebis(indenyl)zirconium dimethyl; methylcyclopentadienyl(cyclopentadienyl)zirconium dihydride; methylcyclopentadienyl(cyclopentadienyl)zirconium dimethyl; methylene (2,7-di-t-butylfluorenyl)(fluorenyl) hafnium dimethyl; methylene (indenyl)(2,7-di-t-butylfluorenyl)hafnium dimethyl; methylene bis(cyclopentadienyl) hafnium dimethyl; methylene bis(cyclopentadienyl)titanium dimethyl; methylene bis(cyclopentadienyl)zirconium dimethyl; methylene bis(fluorenyl)hafnium dimethyl; methylene(cyclopentadienyl (tetramethylcyclopentadienyl) hafnium dimethyl; methylene(cyclopentadienyl (tetramethylcyclopentadienyl)titanium dimethyl; methylene (cyclopentadienyl (tetramethylcyclopentadienyl)zirconium dimethyl; methylene(cyclopentadienyl)(1-fluorenyl) hafnium dihydride; methylene(cyclopentadienyl)(1-fluorenyl)titanium dihydride; methylene(cyclopentadienyl)(1-fluorenyl)zirconium dihydride; methylenebis (cyclopentadienyl)zirconium dihydride; methylenebis (cyclopentadienyl)zirconium dimethyl; methylphenylmethylene bis(fluorenyl)hafnium dimethyl; oxotris(trimethlsilylmethyl)vanadium; pentamethylcyclopentadienyl lanthanum bis(bistrimethyl-silylmethyl); pentamethylcyclopentadienyl titanium trimethyl; pentamethylcyclopentadienyl(cyclopentadienyl)zirconium dihydride; pentamethylcyclopentadienyl(cyclopentadienyl)zirconium dimethyl; pentamethylcyclopentadienyltitanium isopropoxide; pentamethylcyclopentadienyltribenzyltitanium; phenylmethylmethylene(cyclopentadienyl)(9-fluorenyl)zirconium dimethyl; silacyclobutyl(tetramethylcyclopentadienyl)(npropylcyclopentadienyl)zirconium dimethyl; tetrabenzylhafnium; tetrabenzyltitanium; tetrabenzylzirconium; tetrabis(trimethylsilylmethyl)zirconium; tetramethylcyclopentadienyl(cyclopentadienyl)zirconium dimethyl; trifluoromethylcyclopentadienyl(cyclopentadienyl)zirconium dihydride; trifluoromethylcyclopentadienyl(cyclopentadienyl)zirconium dimethyl; trimethylcyclopentadienyl(cyclopentadienyl)zirconium dihydride; trimethylcyclopentadienyl(cyclopentadienyl)zirconium dimethyl; trimethylsilylcyclopentadienyl(cyclopentadienyl)zirconium dihydride; trimethylsilylcyclopentadienyl(cyclopentadienyl)zirconium dimethyl; tris(trimethylsilylmethyl)niobium dichloride; tris(trimethylsilylmethyl)tantalum dichloride; unbridged biscyclopentadienyl compounds such as bis(1-methyl; zirconium bis(acetylacetonate)dimethyl; zirconium butoxytrimethyl; zirconium dibutoxydimethyl; zirconium tetrabenzyl; zirconium tetramethyl

EXAMPLES

The following examples illustrate the foregoing discussion. All parts, proportions, and percentages are by weight unless otherwise indicated. Where necessary, the examples were carried out in dry, oxygen-free environments and solvents. Although the examples may be directed to certain embodiments of the present invention, they do not limit the invention in any specific respect. Certain abbreviations are used to facilitate the description. These include standard chemical abbreviations for the elements and certain commonly accepted abbreviations, such as: Me=methyl, Et=ethyl, n-Pr=normal-propyl, t-Bu=tertiary-butyl, Ph=phenyl, pfp=pentafluorophenyl, Cp=cyclopentadienyl, Ind=indenyl, Flu=fluorenyl, TMS=trimethylsilyl, TES=triethylsilyl and THF (or thf)=tetrahydrofuran.

All molecular weights are weight average molecular weight unless otherwise noted. Molecular weights (weight average molecular weight (Mw)) and number average molecular weight (Mn were measured by Gel Permeation Chromatography (GPC) using a Waters 150 Gel Permeation Chromatograph equipped with a differential refractive index (DRI) and low angle light scattering (LS) detectors. The GPC instrument was calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III'"J. Cazes Ed., Marcel Decker, 1981, page 207. No corrections for column spreading were employed; but data on generally accepted standards, e.g. National Institute of Standards and Technology Polyethylene 1475, demonstrated a precision with 0.2 units for Mw/Mn as calculated from elution times.

Synthesis of $[Li(Et_2O)_3][(o-C_6F_5—C_6F_4)_3BCCC_6H_4F]$: To a cold solution of $FC_6H_4—CCH$ (0.100 milligrams) in diethylether was added 1 equivalent of BuLi (1.6 M, Aldrich). The reaction was stirred at −78° C. for 1 hour. A diethylether solution of $(o-C_6F_5—C_6F_4)_3B$ (1.0 equivalent, 0.796) was added. The ice bath was removed. The reaction was stirred for 3 hours. The solvent was replace with pentane. The resulting white crystalline product collected by filtration (0.77 grams). $^1H$ NMR (Tol.$_{-d8}$, 25° C.): 6.8–6.55 (4H), 3.04 (q, 12), 0.80 (t, 18H). $^{19}F$ NMR: −114.8, −125.6, −137.0, −139.9, −140.5, −157.4, −159.3, −162.9, −165.3, −165.9.

Synthesis of $[tBuDMAH][(o-C_6F_5—C_6F_4)_3BCCC_6H_4F]$: To a methylene chloride solution of $[Li(Et_2O)_3][FC_6H_4—CC—B(C6F4—C_6F_5)_3]$ (0.770 grams) was added a solution of 4-tBuDMAHCl (0.126 grams). After stirring for one hour, the resulting LiCl was removed by filtration. The solvent volume was reduced and the product precipitated out with pentane. The material was placed under vacuum while heating at 65° C. The resulting product is a white solid (0.714 grams). $^1H$ NMR ($CD_2Cl_2$, 25° C.): 7.67 (d, 2H), 7.33 (d, 2H), 6.84 (t, 2H), 6.54 (m, 2H) 3.43 (s, 6H), 1.36 (s, 9H). $^{19}F$ NMR as above.

Synthesis of $[Li(Et_2O)_3][(o-C_6F_5—C_6F_4)_3BCCC_6F_5]$: To a cold solution of $C_6F_5—CCH$ (0.158 milligrams) in diethylether was added 1 equivalent of BuLi (1.6 M, Aldrich). The reaction was allowed to stir at −78° C. for ½ hour. A diethylether solution of $(o-C_6F_5—C_6F_4)_3B$ (1.0 equivalent, 0.789) was added. The ice bath was removed. The reaction was stirred and allowed to reach room temperature. The solvent was replaced with pentane. The resulting white crystalline product was collected by filtration (0.793 grams).

Synthesis of $[tBuDMAH][(o-C_6F_5—C_6F_4)_3BCCC_6F_5]$: To a methylene chloride solution of $[Li(Et_2O)_3][F_5C_6—CC—B(C6F4—C_6F_5)_3]$ (0.785 grams) was added a solution of 4-tBuDMAHCl (0.125 grams). After stirring for one hour, the resulting LiCl was removed by filtration. The solvent volume was reduced and the product precipitated out with pentane. The material was placed under vacuum while heating at 65° C. The resulting product is a white solid (0.750 grams). $^{19}F$ NMR −122.7 (bs, 3F), −135.7(bs, 3F), −137.7 (bs, 2F), −140.0 (dd, 6F), −157.4 (t, 3F), −157.8 (t, 1F), −158.9 (t, 3F), −162.5 (t, 3F), −164.8 (m, 2F), −165.5 (m, 3F), −166.7 (m, 3F).

Ethylene-alpha-Olefin Co-Polymerizations: Polymerizations were performed in a glass-lined, 20-milliliter autoclave reactor equipped with a mechanical stirrer, an external heater for temperature control, a septum inlet and a regulated supply of dry nitrogen and ethylene in an inert atmosphere (Nitrogen) glove box. The reactor was dried and degassed thoroughly at 115° C. The diluent, comonomer, and scavenger were added at room temperature and atmospheric pressure. The reactor was then brought to process pressure and charged with ethylene while stirring at 800 RPM. The activator and catalyst were added via syringe with the reactor at process conditions. The polymerization was continued while maintaining the reaction vessel within 3° C. of the target process temperature and 5 psig of target process pressure (by automatic addition of ethylene on demand) until a fixed uptake of ethylene was noted (corresponding to ca. 0.15 g polymer) or until a maximum reaction time of 20 minutes had passed. The reaction was stopped by pressurizing the reactor to 30 psig above the target process pressure with a gas mixture composed of 5 mol % oxygen in argon. The polymer was recovered by vacuum centrifugation of the reaction mixture. Bulk polymerization activity was calculated by dividing the yield of polymer by the total weight of the catalyst charge by the time in hours and by the absolute monomer pressure in atmospheres. The specific polymerization activity was calculated by dividing the yield of polymer by the total number of millimoles of transition metal contained in the catalyst charge by the time in hours and by the absolute monomer pressure in atmospheres. Pertinent data is summarized in Tables 1 and 2.

TABLE 1

Ethylene/octene copolymerizations[a]

| Act | Cat | Octene wt % | Average Mw | Average Mn | PDI | Actual Quench Time[b] | Yield[c] | Activity[d] |
|---|---|---|---|---|---|---|---|---|
| A | I | 32.9 | 181375 | 88828 | 2 | 52.4 | 0.182 | 625191 |
|  |  | 32 | 178732 | 85578 | 2.1 | 52.4 | 0.196 | 673282 |
|  |  | 31.7 | 155086 | 67920 | 2.3 | 43.2 | 0.222 | 925000 |
|  |  | 32 | 171731 | 80775 |  |  |  | 741158 |
|  | II | 32.2 | 222254 | 109522 | 2 | 57.6 | 0.152 | 475000 |
|  |  | 30.7 | 267994 | 132340 | 2 | 89.1 | 0.123 | 248485 |
|  |  | 33.2 | 279576 | 149540 | 1.9 | 82.6 | 0.123 | 268039 |
|  |  | 32 | 256608 | 130467 |  |  |  | 330508 |
| B | I | 33 | 150433 | 58673 | 2.6 | 40.5 | 0.197 | 875556 |
|  |  | 31.1 | 134682 | 52903 | 2.5 | 39.4 | 0.228 | 1041624 |
|  |  | 30.4 | 141731 | 56949 | 2.5 | 39.3 | 0.212 | 970992 |
|  |  | 32 | 142282 | 56175 |  |  |  | 962724 |
|  | II | 29.6 | 205164 | 97114 | 2.1 | 59 | 0.174 | 530847 |
|  |  | 29.8 | 177655 | 77833 | 2.3 | 55 | 0.195 | 638182 |
|  |  | 30.9 | 173085 | 81183 | 2.1 | 56.4 | 0.199 | 635106 |
|  |  | 30 | 185301 | 85376 |  |  |  | 601379 |
| A | III | 8.7 | 76971 | 24343 | 3.2 | 17 | 0.157 | 1662353 |
|  |  | 9.2 | 67776 | 17424 | 3.9 | 15.8 | 0.177 | 2016456 |
|  |  | 9.6 | 68331 | 15192 | 4.5 | 14.4 | 0.184 | 2300000 |
|  |  | 9 | 71026 | 18986 |  |  |  | 1992936 |
|  | VI | 26.4 | 178610 | 62855 | 2.8 | 43.4 | 0.232 | 962212 |
|  |  | 27.4 | 198547 | 93326 | 2.1 | 45.9 | 0.24 | 941176 |
|  |  | 25.5 | 223047 | 93100 | 2.4 | 53.8 | 0.296 | 990335 |
|  |  | 26 | 200068 | 83094 |  |  |  | 964574 |
| B | III | 5 | 262589 | 169100 | 1.6 | 179.3 | 0.056 | 56219 |
|  |  | 9.2 | 77529 | 26407 | 2.9 | 20.9 | 0.142 | 1222967 |
|  |  | 8.3 | 68917 | 23787 | 2.9 | 18.4 | 0.142 | 1389130 |
|  |  | 8 | 136345 | 73098 |  |  |  | 889439 |
|  | IV | 22.9 | 235119 | 130163 | 1.8 | 49.8 | 0.199 | 719277 |
|  |  | 24.4 | 237804 | 117743 | 2 | 55.1 | 0.212 | 692559 |
|  |  | 25.4 | 729334 | 344833 | 2.1 | 56.3 | 0.214 | 684192 |
|  |  | 24 | 400752 | 197580 |  |  |  | 698676 |
| A | V | 20.7 | 410090 | 231858 | 1.8 | 64.1 | 0.1375 | 386115 |
|  |  | 30.6 | 355705 | 110805 | 3.2 | 81.2 | 0.1534 | 340049 |
|  |  | 19.9 | 325391 | 160052 | 2 | 74.7 | 0.1734 | 417831 |
|  |  | 24 | 363729 | 167572 |  |  |  | 381332 |
|  | VI | 24.8 | 940603 | 370459 | 2.5 | 193.9 | 0.2416 | 224281 |
|  |  | 30.5 | 754657 | 297798 | 2.5 | 150.6 | 0.2394 | 286135 |
|  |  | 30.7 | 826362 | 219550 | 3.8 | 172.9 | 0.2549 | 265367 |
|  |  | 29 | 840541 | 295936 |  |  |  | 258594 |
| B | V | 18 | 549528 | 291361 | 1.9 | 127.3 | 0.0494 | 69851 |
|  |  | 17.9 | 561209 | 291266 | 1.9 | 505.5 | 0.0353 | 12570 |
|  |  | 18 | 555369 | 291314 |  |  |  | 41210 |
|  | VI | 22.9 | 1684479 | 557090 | 3 | 1200.8 | 0.1222 | 18318 |
|  |  | 20.8 | 1593040 | 571907 | 2.8 | 966 | 0.1367 | 25472 |
|  |  | 21 | 1795383 | 533769 | 3.4 | 691.4 | 0.1 | 26034 |
|  |  | 22 | 1690967 | 554255 |  |  |  | 23275 |

[a] = bold entries represent averages
[b] = seconds
[c] = grams of polymer
[d] = grams of polymer/(moles of catalyst × seconds)
A = [DMAH][(C$_6$F$_5$)$_4$B]
B = [tBuDMAH][(o-C$_6$F$_5$—C$_6$F$_4$)$_3$BCCC$_6$H$_4$F]
I = dimethylsilyl bis[2-methyl-4-(o-isopropylphenyl)indenyl] hafnium dimethyl
II = dimethylsilyl bis[2-methyl-4-(o-methylphenyl)indenyl] hafnium dimethyl
III = dimethylsilyl(bis(tetrahydroindenyl) zirconiumdimethyl
IV = dimethylsilyl bis(2-methyl-4-phenylindenyl) zirconium dimethyl
V = dimethylsilyl (bisindenyl) hafnium dimethyl
VI = bis(3,5-triethylsilylphenyl)methylene(cyclopentadienyl)(2,7-di-t-butylfluorenyl) hafnium dimethyl

TABLE 2

Ethylene/octene copolymerizations II[a]

| Act | Cat | Octene wt % | Mw | PDI | Actual Quench Time[b] | Yield[c] | Activity[d] |
|---|---|---|---|---|---|---|---|
| A | VI | 35.8 | 836115.8 | 2.1 | 55.2 | 0.126 | 410870 |
|   |    | 39.1 | 544714.3 | 5.1 | 195.7 | 0.237 | 217987 |
|   |    | 38.6 | 916456.6 | 5.1 | 195.3 | 0.239 | 220276 |
|   |    | 34.4 | 1266512 | 4.3 | 172.2 | 0.242 | 252962 |
|   |    | 36 | 1055700 | 3.8 | 205.4 | 0.236 | 206816 |
|   |    | 35.3 | 1150264 | 3.6 | 195 | 0.229 | 211385 |
|   |    | 39.3 | 483221.5 | 4.7 | 168.3 | 0.231 | 247059 |
|   |    | 34.2 | 1067153 | 3.4 | 198.3 | 0.227 | 206051 |
|   |    | 36.6 | 915017 |  |  |  | 246676 |
|   | VII | 37.5 | 342364.6 | 2.1 | 410.9 | 0.157 | 68776 |
|   |    | 37.5 | 390324.8 | 2.3 | 315.2 | 0.161 | 91942 |
|   |    | 32.4 | 939082.3 | 2 | 455.4 | 0.162 | 64032 |
|   |    | 30.4 | 927221.4 | 1.9 | 411.8 | 0.156 | 68188 |
|   |    | 32 | 682722.6 | 3 | 279 | 0.163 | 105161 |
|   |    | 36.9 | 499312.3 | 2.4 | 269.5 | 0.155 | 103525 |
|   |    | 37.1 | 476973.6 | 2.1 | 378.9 | 0.136 | 64608 |
|   |    | 31.8 | 407695.4 | 2.3 | 245.1 | 0.16 | 117503 |
|   |    | 34.5 | 583212 |  |  |  | 85467 |
| C | VI | 37.8 | 829820.1 | 3.9 | 265.7 | 0.221 | 149718 |
|   |    | 36 | 1093471 | 4 | 323.4 | 0.216 | 120223 |
|   |    | 34.8 | 1808078 | 3.6 | 173.9 | 0.22 | 227717 |
|   |    | 35.6 | 1206888 | 3.7 | 211.4 | 0.225 | 191580 |
|   |    | 38.1 | 989086.7 | 5.1 | 228.1 | 0.226 | 178343 |
|   |    | 38.5 | 643435.2 | 4.6 | 181.6 | 0.214 | 212115 |
|   |    | 33.7 | 1275244 | 3.9 | 197.1 | 0.23 | 210046 |
|   |    | 39.2 | 565589.6 | 4.7 | 224.5 | 0.228 | 182806 |
|   |    | 36.7 | 1051451 |  |  |  | 184068 |
|   | VII | 31.8 | 1064361 | 1.8 | 257.1 | 0.138 | 96616 |
|   |    | 34.7 | 693260.8 | 2.5 | 608 | 0.139 | 41151 |
|   |    | 36.3 | 770664.9 | 2.5 | 428.7 | 0.142 | 59622 |
|   |    | 32.8 | 1017293 | 1.8 | 393.4 | 0.138 | 63142 |
|   |    | 33 | 954648.5 | 2 | 253.8 | 0.141 | 100000 |
|   |    | 36.4 | 728424.9 | 2.5 | 308.9 | 0.145 | 84493 |
|   |    | 32.1 | 1057803 | 1.7 | 309.6 | 0.118 | 68605 |
|   |    | 35.8 | 969186.3 | 2.7 | 413.6 | 0.149 | 64845 |
|   |    | 34.1 | 906955 |  |  |  | 72309 |
| D | VI | 34.1 | 1334561 | 2.7 | 307.6 | 0.207 | 121131 |
|   |    | 27.4 | 2410885 | 3.2 | 260.9 | 0.214 | 147643 |
|   |    | 36.7 | 1040441 | 4.4 | 225.5 | 0.218 | 174013 |
|   |    | 30.2 | 2234909 | 3.3 | 195 | 0.212 | 195692 |
|   |    | 37.7 | 669395.9 | 3.7 | 206.5 | 0.2 | 174334 |
|   |    | 32.3 | 2682394 | 4.1 | 217.9 | 0.206 | 170170 |
|   |    | 37.7 | 990974.6 | 3.3 | 258 | 0.196 | 136744 |
|   |    | 32.6 | 1430860 | 3 | 178.3 | 0.195 | 196859 |
|   |    | 33.6 | 1599302 |  |  |  | 164573 |
|   | VII | 34.8 | 1053676 | 2.6 | 897.7 | 0.137 | 27470 |
|   |    | 32.6 | 922797.1 | 3.7 | 805.8 | 0.136 | 30380 |
|   |    | 36 | 779452.2 | 2.1 | 496.2 | 0.139 | 50423 |
|   |    | 31.9 | 1157734 | 1.8 | 552.8 | 0.145 | 47214 |
|   |    | 32.5 | 1193431 | 1.7 | 503 | 0.137 | 49026 |
|   |    | 30 | 1226141 | 1.7 | 559.7 | 0.138 | 44381 |
|   |    | 35 | 962302.9 | 2.8 | 434 | 0.14 | 58065 |
|   |    | 33.8 | 1199827 | 2.1 | 544 | 0.146 | 48309 |
|   |    | 33.3 | 1061920 |  |  |  | 44409 |

A = [DMAH][(C$_6$F$_5$)$_4$B]
B = [tBuDMAH][(o-C$_6$F$_5$—C$_6$F$_4$)$_3$BCCC$_6$H$_4$F]
C = [DMAH][tetrakis(perfluoronaphthyl)borate]
D = [tBuDMAH][(o-C$_6$F$_5$—C$_6$F$_4$)$_3$BCCC$_6$F$_5$]
I = dimethylsilyl bis[2-methyl-4-(o-isopropylphenyl)indenyl] hafnium dimethyl
II = dimethylsilyl bis[2-methyl-4-(o-methylphenyl)indenyl] hafnium dimethyl
III = dimethylsilyl(bis(tetrahydroindenyl) zirconiumdimethyl
IV = dimethylsilyl bis(2-methyl-4-phenylindenyl) zirconium dimethyl
V = dimethylsilyl (bisindenyl) hafnium dimethyl
VI = bis(3,5-triethylsilylphenyl)methylene(cyclopentadienyl)(2,7-di-t-butylfluorenyl) hafnium dimethyl
VII = diphenylmethyleneecyclopentadienylfluorenyl hafnium dimethyl While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A composition of matter comprising
   (a) a cation; and
   (b) a triel moiety comprising at least one triel connected to
      (i) three bulky aryl ligands at least one being fluorinated and
      (ii) an anion-forming ligand comprising a spacing group and capping group, where the spacing group is —C≡C— and where the anion-forming ligand is an acetylene-aryl group.

2. The composition of claim 1 wherein the triel is boron.

3. The composition of claim 1 wherein the triel is aluminum.

4. The composition of claim 1 wherein the capping group is selected from fluorophenyl, perfluorophenyl, 3,5-bis(trifluoromethyl)phenyl, trifluorophenyl, (trifluoromethyl)phenyl, naphth-1-yl, naphth-2-yl, perfluoronaphth-1-yl, perfluoronaphth-2-yl, (trifluoro)naphth-1-yl, (trifluoro)naphth-2-yl, (trifluoromethyl)naphth-1-yl, (trifluoromethyl)naphth-2-yl, anthr-1-yl, anthr-2-yl, perfluoroanthr-1-yl, perfluoroanthr-2-yl, (trifluoro)anthr-1-yl, (trifluoro)anthr-2-yl, (trifluoromethyl)anthr-1-yl, (trifluoromethyl)anthr-2-y, phenanthr-1-yl, phenanthr-2-yl, perfluorophenanthr-1-yl, perfluorophenanthr-2-yl, (trifluoro)phenanthr-1-yl, (trifluoro)phenanthr-2-yl, (trifluoromethyl)phenanthr-1-yl, (trifluoromethyl)phenanthr-2-yl, biphen-3-yl, biphen-4-yl, perfluorobiphen-3-yl, perfluorobiphen-4-yl, (trifluoro)biphen-3-yl, (trifluoro)biphen-4-yl, (trifluoromethyl)biphen-3-yl, and (trifluoromethyl)biphen-4-yl.

5. The composition of claim 1 wherein the capping group is selected from fluorophenyl, perfluorophenyl, 3,5-bis(trifluoromethyl)phenyl, trifluorophenyl, (trifluoromethyl)phenyl, naphth-1-yl, naphth-2-yl, perfluoronaphth-1-yl, perfluoronaphth-2-yl, (trifluoro)naphth-1-yl, (trifluoro)naphth-2-yl, (trifluoromethyl)naphth-1-yl, (trifluoromethyl)naphth-2-yl, biphen-3-yl, biphen-4-yl, perfluorobiphen-3-yl, perfluorobiphen-4-yl, (trifluoro)biphen-3-yl, (trifluoro)biphen-4-yl, (trifluoromethyl)biphen-3-yl, and (trifluoromethyl)biphen-4-yl.

6. The composition of claim 1 wherein the anion-forming ligand is represented by the following formula:

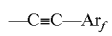

wherein Ar$_f$ is a fluorinated bulky aryl group.

7. The composition of claim 6 wherein Ar$_f$ is selected from fluorophenyl, perfluorophenyl, 3,5-bis(trifluoromethyl)phenyl, trifluorophenyl, (trifluoromethyl)phenyl, naphth-1-yl, naphth-2-yl, perfluoronaphth-1-yl, perfluoronaphth-2-yl, (trifluoro)naphth-1-yl, (trifluoro)naphth-2-yl, (trifluoromethyl)naphth-1-yl, (trifluoromethyl)naphth-2-yl, anthr-1-yl, anthr-2-yl, perfluoroanthr-1-yl, perfluoroanthr-2-yl, (trifluoro)anthr-1-yl, (trifluoro)anthr-2-yl, (trifluoromethyl)anthr-1-yl, (trifluoromethyl)anthr-2-y, phenanthr-1-yl, phenanthr-2-yl, perfluorophenanthr-1-yl, perfluorophenanthr-2-yl, (trifluoro)phenanthr-1-yl, (trifluoro)phenanthr-2-yl, (trifluoromethyl)phenanthr-1-yl, (trifluoromethyl)phenanthr-2-yl, biphen-3-yl, biphen-4-yl, perfluorobiphen-3-yl, perfluorobiphen-4-yl, (trifluoro)biphen-3-yl, (trifluoro)biphen-4-yl, (trifluoromethyl)biphen-3-yl, and (trifluoromethyl)biphen-4-yl.

8. The composition of claim 1 wherein the activating cation is one of anilinium and ammonium cations, trityl carbenium cations, Group-11 metal cations, silylium cations, and the cations of the hydrated salts of Group-1 or -2 metals.

9. The composition of claim 1 wherein:
(a) the activating cation is substituted or unsubstituted dimethylanilinium; and
(b) the triel moiety is tris(perfluorobiphen-2-yl)(2-(perfluoroaryl)ethyn-1-yl)borate, wherein aryl is selected from phenyl, naphthyl, biphenyl, anthryl, and phenanthryl.

10. The composition of claim 9 wherein the triel moiety is tris(perfluorobiphen-2-yl)(2-perfluorophenylethyn-1-yl)borate.

11. The composition of claim 1 wherein at least one bulky aryl ligand is selected from fluorinated biphenyl, phenyl, indenyl, naphthyl, fluorenyl, pyrenyl, anthryl, phenanthrenyl, azulenyl, aceanthrylenyl, acenaphthylenyl, or acephenanthrylenyl radicals.

12. The composition of claim 1 wherein the bulky aryl ligand is represented by one of the formulas shown below provided that the bulky aryl ligand has had one hydrogen atom replaced by a fluorine atom:

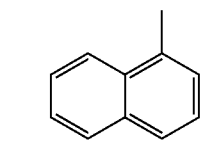
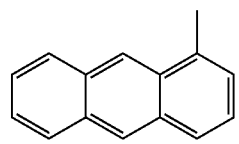
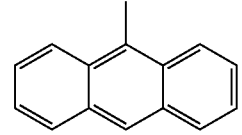
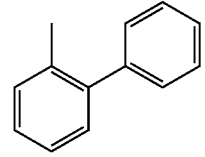
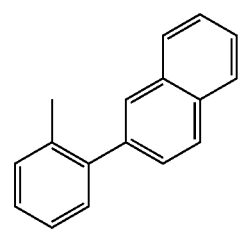
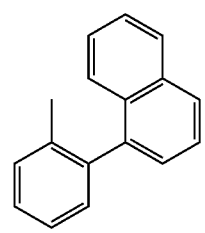
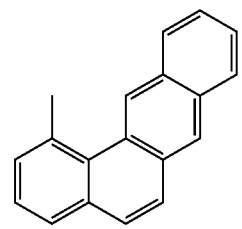
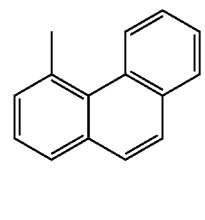

-continued

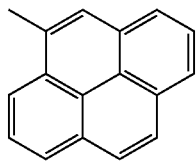
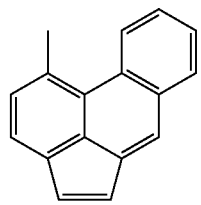
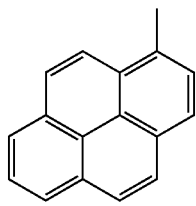
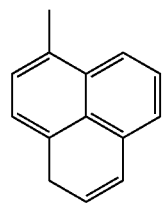
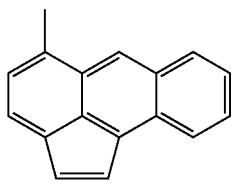
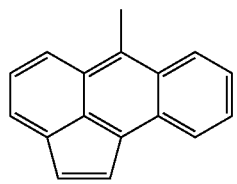
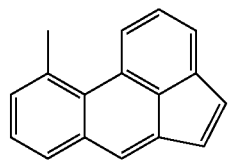
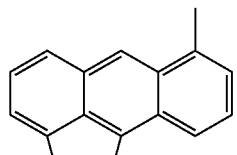
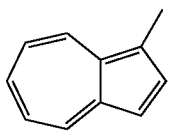
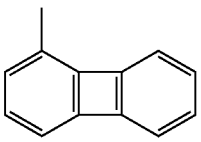
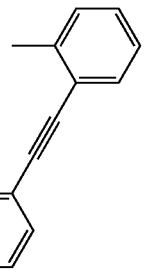
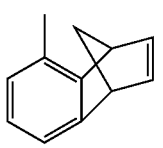
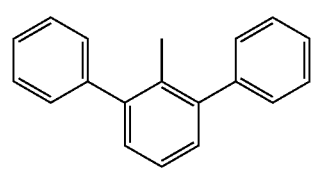

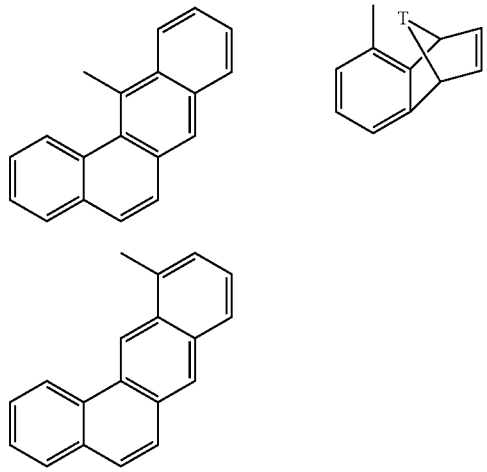

wherein T is selected from S, O, or N—R and R is a $C_1$–$C_{50}$ hydrocarbyl.

13. The composition of claim 12 wherein all bulky aryl ligands are the same.

14. The composition of claim 12 wherein the bulky aryl ligands are perfluorinated.

15. The composition of claim 12 wherein the bulky aryl ligands have had at least three hydrogen atoms replaced by fluorine atoms.

16. The composition of claim 12 wherein the bulky aryl ligands have had at least five hydrogen atoms replaced by fluorine atoms.

17. The composition of claim 12 wherein the bulky aryl ligands have had at least seven hydrogen atoms replaced by fluorine atoms.

18. A composition of matter having the following formula:

$$[[R]_3[B]CCAr_f]^-$$

wherein
(a) B is boron;
(b) C is carbon;
(c) $Ar_f$ is a fluorinated aryl group; and
(d) R are independently selected from fluorinated biphenyl, phenyl, indenyl, naphthyl, fluorenyl, or pyrenyl radicals.

19. A composition of matter comprising
(a) a cation; and
(b) a Group-13 moiety comprising at least one Group-13 atom connected to:
    (i) at least one fluorinated aryl group; and
    (ii) at least one acetylene-aryl moiety.

20. A cocatalyst comprising:
(a) an activating cation; and
(b) a Group-13 moiety that comprises at least one Group-13 atom connected to
    (i) at least one fluorinated aryl group; and
    (ii) at least one acetylene-aryl moiety.

21. The cocatalyst of claim 20 wherein at least one aryl group is selected from fluorinated biphenyl, phenyl, indenyl, naphthyl, fluorenyl, or pyrenyl radicals.

22. The cocatalyst of claim 20 wherein the Group-13 atom is boron.

23. The cocatalyst of claim 20 wherein at least one aryl group is perfluorinated.

24. The cocatalyst of claim 20 wherein each of the aryl groups is the same.

25. The cocatalyst of claim 20 wherein the Group-13 moiety comprises three aryl groups.

26. The cocatalyst of claim 20 wherein the acetylene-aryl moiety comprises the following formula:

—C≡C—$Ar_f$ wherein Arf is a fluorinated aryl group.

27. The cocatalyst of claim 26 wherein Arf is selected from fluorophenyl, perfluorophenyl, 3,5-bis(trifluoromethyl)phenyl, trifluorophenyl, (trifluoromethyl)phenyl, naphth-1-yl, naphth-2-yl, perfluoronaphth-1-yl, perfluoronaphth-2-yl, (trifluoro)naphth-1-yl, (trifluoro)naphth-2-yl, (trifluoromethyl)naphth-1-yl, (trifluoromethyl)naphth-2-yl, anthr-1-yl, anthr-2-yl, perfluoroanthr-1-yl, perfluoroanthr-2-yl, (trifluoro)anthr-1-yl, (trifluoro)anthr-2-yl, (trifluoromethyl)anthr-1-yl, (trifluoromethyl)anthr-2-y, phenanthr-1-yl, phenanthr-2-yl, perfluorophenanthr-1-yl, perfluorophenanthr-2-yl, (trifluoro)phenanthr-1-yl, (trifluoro)phenanthr-2-yl, (trifluoromethyl)phenanthr-1-yl, (trifluoromethyl)phenanthr-2-yl, biphen-3-yl, biphen-4-yl, perfluorobiphen-3-yl, perfluorobiphen-4-yl, (trifluoro)biphen-3-yl, (trifluoro)biphen-4-yl, (trifluoromethyl)biphen-3-yl, and (trifluoromethyl)biphen-4-yl.

28. The cocatalyst of claim 20 wherein the Group-13 atom is boron and wherein the Group-13 atom connects to three of the same aryl groups and to one acetylene-aryl moiety.

29. The cocatalyst of claim 20, wherein the activating cation is one of anilinium and ammonium cations, trityl carbenium cations, Group-11 metal cations, silylium cations, and the cations of the hydrated salts of Group-1 or -2 metals.

30. The cocatalyst of claim 20 wherein:
(a) the activating cation is substituted or unsubstituted dimethylanilinium; and
(b) the Group-13 moiety is tris(perfluorobiphen-2-yl)(2-(perfluoroaryl)ethyn-1-yl)borate, wherein aryl is selected from phenyl, naphthyl, biphenyl, anthryl, and phenanthryl.

31. The cocatalyst of claim 20 wherein the Group-13 moiety is tris(perfluorobiphen-2-yl)(2-perfluorophenylethyn-1-yl)borate.

32. A catalyst system comprising the contact product of a catalyst precursor and the cocatalyst of claim 20.

33. An activator comprising:
(a) an activating cation selected from anilinium and ammonium cations, trityl carbenium cations, Group-11 metal cations, silylium cations, and the cations of the hydrated salts of Group-1 or -2 metals; and
(b) a triel moiety that comprises at least one triel connected to
    (i) three bulky aryl ligands at least one being fluorinated and
    (ii) an anion-forming ligand comprising a spacing group and a capping group, where the spacing group is —C≡C— and where the anion-forming ligand is an acetylene-aryl group.

34. An activator comprising:
(a) dimethylanilinium; and
(b) a triel moiety that comprises at least one triel connected to
    (i) three bulky aryl ligands and
    (ii) an anion-forming ligand, comprising a spacing group and a capping group, where the spacing group is —C≡C— and where the anion-forming ligand is an acetylene-aryl group.

35. An activator comprising:
(a) an activating cation; and
(b) a triel moiety that comprises at least one triel connected to
   (i) three bulky aryl ligands at least one being fluorinated independently selected from fluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

36. An activator comprising:
(a) an activating cation; and
(b) a triel moiety that comprises at least one triel connected to
   (i) three bulky aryl ligands at least one being fluorinated wherein the bulky ligands are the same and are selected from fluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

37. An activator comprising:
(a) an activating cation; and
(b) a triel moiety that comprises at least one triel connected to
   (i) three bulky aryl ligands at least one being fluorinated wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

38. An activator comprising:
(a) an activating cation selected from anilinium and ammonium cations, trityl carbenium cations, Group-11 metal cations, silylium cations, and the cations of the hydrated salts of Group-1 or -2 metals; and
(b) a triel moiety that comprises at least one triel connected to
   (i) three bulky aryl ligands at least one being fluorinated wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

39. An activator comprising:
(a) dimethylanilimium; and
(b) a triel moiety that comprises at least one triel connected to
   (i) three bulky aryl ligands wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

40. An activator comprising:
(a) an activating cation selected from anilinium and ammonium cations, trityl carbenium cations, Group-11 metal cations, silylium cations, and the cations of the hydrated salts of Group-1 or -2 metals; and
(b) a moiety that comprises at least one boron connected to
   (i) three bulky aryl ligands at least one being fluorinated and
   (ii) an anion-forming ligand, comprising a spacing group and a capping group, where the spacing group is —C≡C— and where the anion-forming ligand is an acetylene-aryl group.

41. An activator comprising:
(a) dimethylanilinium; and
(b) a moiety that comprises at least one boron connected to
   (i) three bulky aryl ligands and
   (ii) an anion-forming ligand, comprising a spacing group and a capping group, where the spacing group is —C≡C— and where the anion-forming ligand is an acetylene-aryl group.

42. An activator comprising:
(a) an activating cation; and
(b) a moiety that comprises at least one boron connected to
   (i) three bulky aryl ligands at least one being fluorinated independently selected from fluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

43. An activator comprising:
(a) an activating cation; and
(b) a moiety that comprises at least one boron connected to
   (i) three bulky aryl ligands at least one being fluorinated wherein the bulky ligands are the same and are selected from fluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
   (ii) an anion-forming ligand, comprising a spacing group and a capping group, where the spacing group is —C≡C— and where the anion-forming ligand is an acetylene-aryl group.

44. An activator comprising:
(a) an activating cation; and
(b) a moiety that comprises at least one boron connected to
   (i) three bulky aryl ligands at least one being fluorinated wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and (ii) an anion-forming ligand, comprising a spacing group and a capping group, where the spacing group is —C≡C— and where the anion-forming ligand is an acetylene-aryl group.

45. An activator comprising:
(a) an activating cation selected from anilinium and ammonium cations, trityl carbenium cations, Group-11 metal cations, silylium cations, and the cations of the hydrated salts of Group-1 or -2 metals; and
(b) a moiety that comprises at least one boron connected to
  (i) three bulky aryl ligands at least one being fluorinated wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
  (ii) an anion-forming ligand, comprising a spacing group and a capping group, where the spacing group is —C≡C— and where the anion-forming ligand is an acetylene-aryl group.

46. An activator comprising:

(a) dimethylanilimium; and
(b) a moiety that comprises at least one boron connected to
  (i) three bulky aryl ligands wherein the bulky ligands are the same and are selected from perfluorinated biphenyl, phenyl, indenyl, naphthyl, fluorenyl, pyrenyl, anthryl, phenanthreneyl, azulenyl, aceanthrylenyl, acenaphthylenyl, or acephenanthrylenyl radicals and
  (ii) an anion-forming ligand, comprising a spacing group and a capping group, where the spacing group is —C≡C— and where the anion-forming ligand is an acetylene-aryl group.

* * * * *